(12) United States Patent
Lee et al.

(10) Patent No.: US 11,773,109 B2
(45) Date of Patent: Oct. 3, 2023

(54) COMPOSITION FOR HARDENING SOFT TISSUE

(71) Applicants: The Catholic University of Korea Industry—Academic Cooperation Foundation, Seoul (KR); Korea Research Institute of Chemical Technology, Daejeon (KR)

(72) Inventors: Sang Chul Lee, Daejeon (KR); Say June Kim, Daejeon (KR); Kwan Young Jeong, Daejeon (KR); Ok Hee Kim, Chungcheongnam-do (KR); Seok Jun Jo, Jeollabuk-do (KR); Min Jin Yoo, Gyeongsangnam-do (KR)

(73) Assignees: THE CATHOLIC UNIVERSITY OF KOREA INDUSTRY-ACADEMIC COOPERATION FOUNDATION; KOREA RESEARCH INSTITUTE OF CHEMICAL TECHNOLOGY

( * ) Notice: Subject to any disclaimer, the term of this patent is extended or adjusted under 35 U.S.C. 154(b) by 0 days.

(21) Appl. No.: 16/925,043

(22) Filed: Jul. 9, 2020

(65) Prior Publication Data
US 2020/0339601 A1 Oct. 29, 2020

Related U.S. Application Data

(62) Division of application No. 16/325,073, filed as application No. PCT/KR2017/008743 on Aug. 11, 2017, now Pat. No. 10,745,417.

(30) Foreign Application Priority Data

Aug. 12, 2016 (KR) .......... 10-2016-0102895

(51) Int. Cl.
| | | |
|---|---|---|
| C07D 499/21 | (2006.01) | |
| C07D 499/06 | (2006.01) | |
| G01N 33/483 | (2006.01) | |
| G01N 33/50 | (2006.01) | |
| C07D 215/20 | (2006.01) | |

(52) U.S. Cl.
CPC ......... *C07D 499/21* (2013.01); *C07D 499/06* (2013.01); *G01N 33/4833* (2013.01); *G01N 33/50* (2013.01); *C07D 215/20* (2013.01)

(58) Field of Classification Search
CPC .................................................. C07D 499/88
See application file for complete search history.

(56) References Cited

U.S. PATENT DOCUMENTS

| | | | | |
|---|---|---|---|---|
| 3,528,965 A | * | 9/1970 | Doyle .................. | C07D 499/00 540/316 |
| 3,855,233 A | | 12/1974 | Dolfini et al. | |
| 4,377,590 A | * | 3/1983 | Myers .................... | A61P 31/04 540/335 |
| 4,788,282 A | | 11/1988 | Deziel | |
| 2019/0315770 A1 | | 10/2019 | Lee et al. | |

FOREIGN PATENT DOCUMENTS

| | | |
|---|---|---|
| CN | 1879620 | 12/2006 |
| CN | 103483445 | 1/2014 |
| DE | 2412525 | 9/1974 |
| EP | 0013663 | 7/1980 |
| EP | 0170192 | 2/1986 |
| JP | S48-091087 | 11/1973 |
| JP | S49-048723 | 12/1974 |
| JP | S51-80891 | 7/1976 |
| JP | S52-23091 | 2/1977 |
| JP | S52-78993 | 7/1977 |
| JP | H04-108793 | 4/1992 |
| JP | 2012-530697 | 12/2012 |
| KR | 10-2004-0038905 | 5/2004 |

OTHER PUBLICATIONS

Kirchner et al. (Journal of Organic Chemistry, 1949, 14, pp. 388-393).*
Reeves et al. (Infection, 1979, 7(5), 425-433).*
Ganboa et al. "Phase-Transfer Esterification of the Alkali Metal Salts of Cephalosporins and Penicillins," Synthesis, 1986, pp. 52-54.
Jeffrey et al. Homogenous, Palladium(O)-Catalyzed Exchange Deprotection of Allylic Esters, Carbonates, and Carbamates, Journal of Organic Chemistry, American Chemical Society, US. Jan. 1982, vol. 47, pp. 587-590.
Kirchner et al. "The Use of Diazo Compounds In The Preparation Of Some Benzylpenicillin Esters," Contribution from the Sterling-Winthrop Research Institute, Dec. 1948, pp. 388-393 [retrieved online from: pubs.acs.org/doi/pdf/10.1021/jo01155a008].
Manhas et al. "A Convenient Synthesis of Esters of 6-Aminopenicillanic Acid," Synthesis, Jul. 1983, pp. 549-552.
Ramaiah "A New Convenient Method for Esterification Using the Ph3P/CCl4 System," The Journal of Organic Chemistry, 1985, vol. 50, pp. 4991-4993.
International Search Report prepared by the Korean Intellectual Property Office dated Dec. 22, 2017, for International Application No. PCT/KR2017/008743.

(Continued)

*Primary Examiner* — Susanna Moore
(74) *Attorney, Agent, or Firm* — Sheridan Ross P.C.

(57) ABSTRACT

The present invention relates to various compounds capable of temporarily hardening soft tissue for surgical suturing of the soft tissue. The compounds according to the present invention can temporarily increase the hardness or tension of soft tissue, thereby improving the suturing efficiency during suturing of the soft tissue, thereby preventing aftereffects or the like from occurring due to insufficient anastomosis. In addition, the compounds according to the present invention can temporarily increase the hardness or tension of soft tissue, particularly pancreas, thereby increasing the suturing efficiency during pancreaticoduodenectomy and effectively preventing pancreatic leakage.

5 Claims, 4 Drawing Sheets

(56) References Cited

OTHER PUBLICATIONS

Supplementary Search Report for European Patent Application No. 17839857.4, dated Feb. 11, 2020, 18 pages.
Official Action with English Translation for Japan Patent Application No. 2019-50773, dated Jan. 30, 2020, 12 pages.
Official Action for U.S. Appl. No. 16/325,073, dated Feb. 4, 2020 9 pages Restriction Requirement.
Notice of Allowance for U.S. Appl. No. 16/325,073, dated Apr. 13, 2020 10 pages.
Official Action with English Translation for China Patent Application No. 201780060885.6, dated Dec. 9, 2020, 11 pages.
English Translation of Official Action for Japan Patent Application No. 2021-093468, dated Jul. 5, 2022, 6 pages.

* cited by examiner

[FIG. 1]
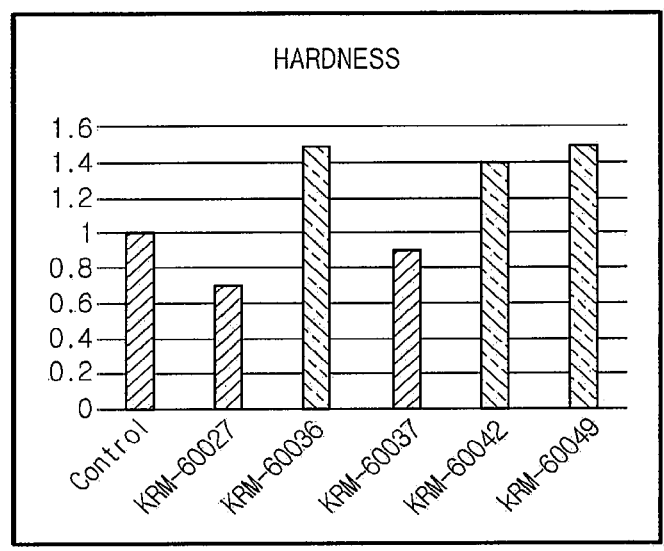
[FIG. 2]
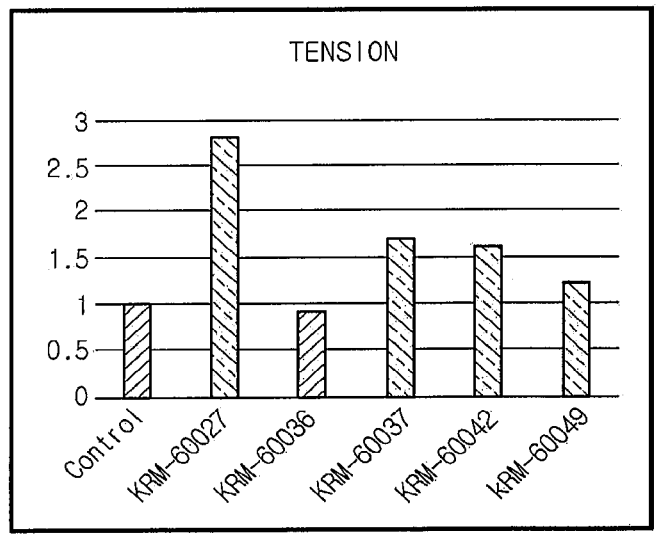

[FIG. 3]
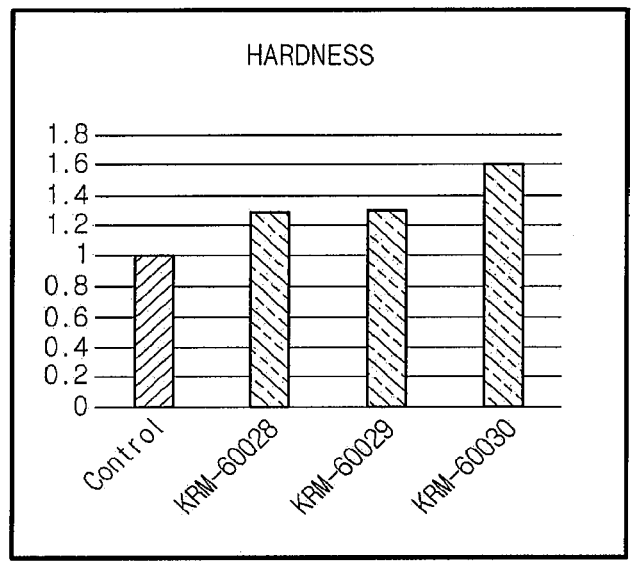
[FIG. 4]
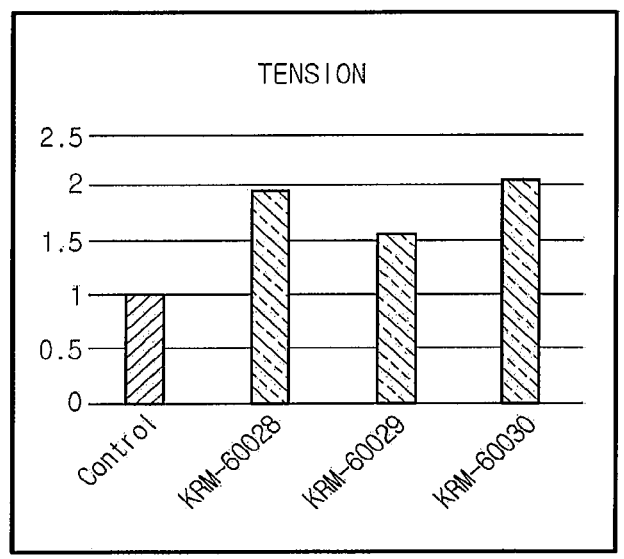

[FIG. 5]
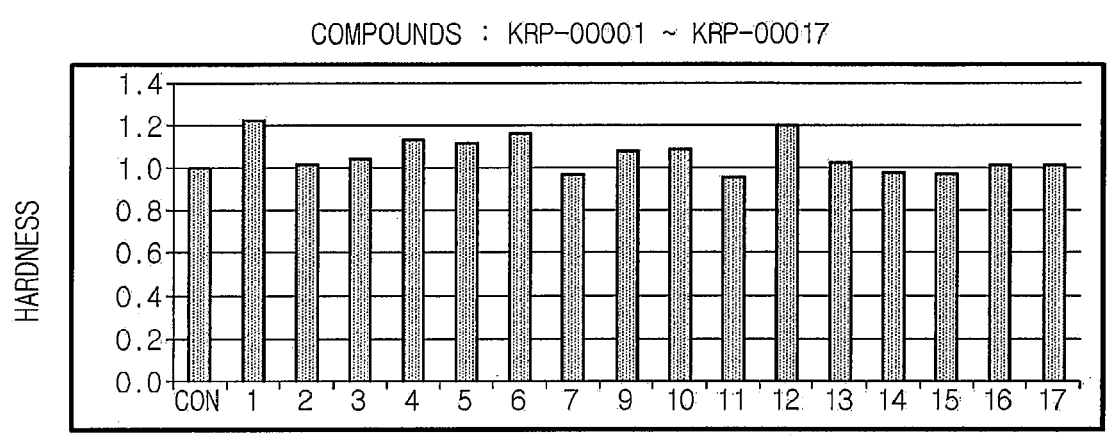
[FIG. 6]
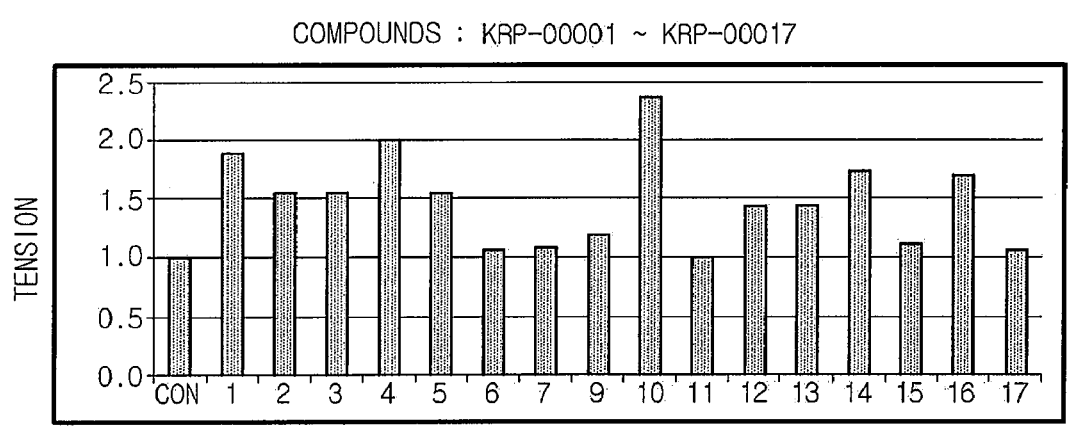

[FIG. 7]
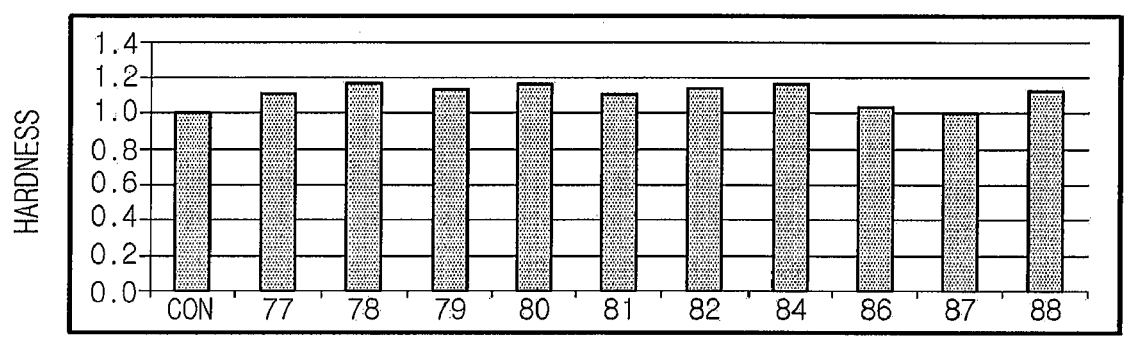
[FIG. 8]
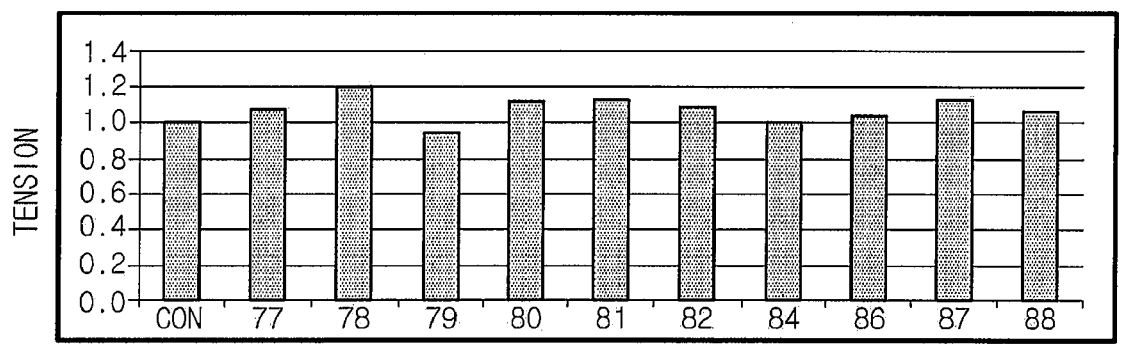

COMPOSITION FOR HARDENING SOFT TISSUE

CROSS REFERENCE TO RELATED APPLICATIONS

This application is a divisional application of U.S. Patent Application Ser. No. 16/325,073, filed Feb. 12, 2019, which is a national stage application under 35 U.S.C. 371 and claims the benefit of PCT Application No. PCT/KR2017/008743 having an international filing date of 11 Aug. 2017, which designated the United States, which PCT application claimed the benefit of Republic of Korea Application No. 10-2016-0102895, filed 12 Aug. 2016, the disclosures of each of which are incorporated herein by reference in their entireties.

TECHNICAL FIELD

The present invention relates to compounds capable of temporarily hardening soft tissue for surgical suturing of the soft tissue.

BACKGROUND ART

Pancreas is an organ located behind the stomach. It secretes a variety of digestive enzymes which promote degradation of the carbohydrates, proteins and fats that passed through the stomach. Also, it produces important hormones such as insulin, glucagon and the like. If the secretion of digestive enzymes from the pancreas is insufficient, the uptake of nutrients becomes insufficient. In addition, the secretion of insulin and glucagon regulates intravascular glucose levels. Studies on the mechanisms that control the production and secretion of these various enzymes and hormones have become important topics in relation to nutrition and diverse diseases, such as diabetes, obesity and the like.

Major diseases that occur in relation to the pancreas include pancreatic cancer, pancreatitis, diabetes and the like. Diabetes is a risky disease that occurs when insulin secretion in the pancreas declines or resistance to insulin action in other tissues occurs, leading to various complications due to elevated blood glucose levels. In addition, pancreatic cancer is known to be a disease that has the highest mortality rate among malignant tumors and has a poor prognosis.

The most common treatment methods for the treatment of diseases related to the pancreas are performed by the administration or intravenous infusion of analgesics, antibiotics, anticancer drugs, or the like. In severe cases, pancreaticoduodenectomy is performed, which treats the diseases by surgery.

The pancreaticoduodenectomy has been widely distributed by Whipple et al. since successful pancreaticoduodenectomy was first introduced by Kausch in 1912. The pancreaticoduodenectomy is an important surgical procedure that is applied to radical treatment of Vater periampullary cancer which occurs in the pancreas, head, common bile duct, duodenal ampulla or the like, but it is a surgical method having a high possibility of developing postoperative complications. Until the 1970s, the pancreaticoduodenectomy was reported to have a postoperative mortality rate of about 20%. Recently, pancreaticoduodenectomy has been reported to have a mortality rate of 5% or less due to advances in surgical technology, anesthetic technology, patient management before and after surgery, nutritional management, and the like.

However, despite the dramatic decrease in mortality rate, the incidence of postoperative complications has been reported to be 40-50% even in recent years. Among these complications, the incidence of pancreatic leakage, which is closely related to mortality rate, has been reported to be still 10-20%. It was found that pancreatic leakage, when occurred, could cause intraperitoneal hemorrhage, abscess or the resulting sepsis, and the mortality rate associated with it was also high.

According to several reports, it is known that the diameter of the pancreatic duct, the consistency of the pancreatic parenchyma, and the like, are risk factors that are involved in the occurrence of pancreatic leakage. Here, regarding the consistency of the pancreatic parenchyma, the pancreas parenchyma remaining after pancreatectomy is very soft, so there is a high risk of crushing the tissue at the time of suturing, and hence a high level of skill is required for suturing. Even after the suturing, anastomosis is not properly achieved, so that pancreatic juice flows out through the gap, causing the pancreatic leakage.

Accordingly, recently, pancreas-jejunum anastomosis, pancreas-stomach anastomosis, pancreatic duct-mucosal anastomosis, dunking, stent implantation and the like have been proposed to prevent the occurrence of postoperative pancreatic leakage. In addition to these surgical suturing methods, somatostatin, fibrin glue or the like has also been proposed.

The present inventors have found that novel compounds synthesized using the structure of existing antibiotics as a basic skeleton can temporarily harden the pancreas, and thus can increase the efficiency of suturing during pancreatic surgery such as pancreaticoduodenectomy, thereby completing the present invention.

DISCLOSURE

Technical Problem

The present inventors have developed novel compounds capable of temporarily hardening the pancreas, making it possible to more efficiently suture the pancreas in order to prevent pancreatic leakage from occurring after pancreaticoduodenectomy. As a result, the present inventors have found that compound derivatives according to the present invention can temporarily increase the hardness and tension of soft tissue such as the pancreas, thereby completing the present invention.

Therefore, it is an object of the present invention to provide a novel compound represented by formula 1 or a pharmaceutically acceptable salt thereof.

Another object of the present invention is to provide a method for preparing the compound.

Still another object of the present invention is to provide a pharmaceutical composition for hardening soft tissue.

Still another object of the present invention is to provide a pharmaceutical composition for hardening the pancreas.

Still another object of the present invention is to provide a pharmaceutical composition for preventing pancreatic leakage.

Still another object of the present invention is to provide a method for screening a compound for hardening soft tissue.

Technical Solution

Hereinafter, various embodiments described herein will be described with reference to figures. In the following description, numerous specific details are set forth, such as specific configurations, compositions, and processes, etc., in order to provide a thorough understanding of the present invention. However, certain embodiments may be practiced without one or more of these specific details, or in combination with other known methods and configurations. In other instances, known processes and preparation techniques have not been described in particular detail in order to not unnecessarily obscure the present invention. Reference throughout this specification to "one embodiment" or "an embodiment" means that a particular feature, configuration, composition, or characteristic described in connection with the embodiment is included in at least one embodiment of the present invention. Thus, the appearances of the phrase "in one embodiment" or "an embodiment" in various places throughout this specification are not necessarily referring to the same embodiment of the present invention. Additionally, the particular features, configurations, compositions, or characteristics may be combined in any suitable manner in one or more embodiments.

In accordance with one embodiment of the present invention, there is provided a compound represented by the following formula 1 or a pharmaceutically acceptable salt or hydrate thereof:

[Formula 1]

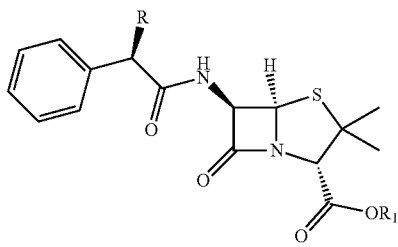

wherein

R is hydrogen or N(R')(R");

R' and R" are each independently hydrogen, a $C_{1-6}$ alkyl group or a $C_{1-6}$ alkenyl group;

$R_1$ is hydrogen or a $C_{1-6}$ alkyl group;

the $C_{1-6}$ alkyl group of $R_1$ is unsubstituted or substituted with $R_2$;

$R_2$ is selected from the group consisting of a $C_{1-6}$ alkenyl group, a $C_{3-7}$ cycloalkyl group, a cyano group, a $C_{1-6}$ alkyl group, a $C_{6-10}$ aryl group, —$OR_3$ and —$COOR_4$;

the aryl group of $R_2$ is unsubstituted or substituted with halogen;

$R_3$ is —$(CH_2)_m OR_5$;

m is an integer ranging from 0 to 3; and $R_4$ and $R_5$ are each independently a $C_{1-6}$ alkyl group.

In one embodiment of the present invention, the compound of formula 1 or the pharmaceutically acceptable salt thereof may preferably be one or more selected from among the compounds shown in Table 1 below.

TABLE 1

| Structural formula | Compound name | Name |
| --- | --- | --- |
|  | (2S,5R,6R)-3,3-dimethyl-7-oxo-6-(2-phenylacetamido)-4-thia-1-azabicyclo[3.2.0]heptane-2-carboxylic acid | — |
|  | Allyl (2S,5R,6R)-3,3-dimethyl-7-oxo-6-(2-phenylacetamido)-4-thia-1-azabicyclo[3.2.0]heptane-2-carboxylate | KRM-60028 |
|  | Cyclohexylmethyl (2S,5R,6R)-3,3-dimethyl-7-oxo-6-(2-phenylacetamido)-4-thia-1-azabicyclo[3.2.0]heptane-2-carboxylate | KRM-60029 |
|  | 3-cyanopropyl (2S,5R,6R)-3,3-dimethyl-7-oxo-6-(2-phenylacetamido)-4-thia-1-azabicyclo[3.2.0]heptane-2-carboxylate | KRM-60030 |

TABLE 1-continued

| Structural formula | Compound name | Name |
|---|---|---|
| | 3-(tert-butoxy)-3-oxopropyl (2S,5R,6R)-3,3-dimethyl-7-oxo-6-(2-phenylacetamido)-4-thia-1-azabicyclo[3.2.0]heptane-2-carboxylate | KRM-60077 |
| | Isobutyl (2S,5R,6R)-3,3-dimethyl-7-oxo-6-(2-phenylacetamido)-4-thia-1-azabicyclo[3.2.0]heptane-2-carboxylate | KRM-60078 |
| | 2-fluorobenzyl (2S,5R,6R)-3,3-dimethyl-7-oxo-6-(2-phenylacetamido)-4-thia-1-azabicyclo[3.2.0]heptane-2-carboxylate | KRM-60079 |
| | 2-(2-ethoxyethoxy)ethyl (2S,5R,6R)-3,3-dimethyl-7-oxo-6-(2-phenylacetamido)-4-thia-1-azabicyclo[3.2.0]heptane-2-carboxylate | KRM-60080 |
| | (2S,5R,6R)-6-((R)-2-amino-2-phenylacetamido)-3,3-dimethyl-7-oxo-4-thia-1-azabicyclo[3.2.0]heptane-2-carboxylic acid | — |
| | (2S,5R,6R)-cyclohexylmethyl 6-((R)-2-amino-2-phenylacetamido)-3,3-dimethyl-7-oxo-4-thia-1-azabicyclo[3.2.0]heptane-2-carboxylate | — |

TABLE 1-continued

| Structural formula | Compound name | Name |
|---|---|---|
| | (2S,5R,6R)-3-cyanopropyl 6-((R)-2-amino-2-phenylacetamido)-3,3-dimethyl-7-oxo-4-thia-1-azabicyclo[3.2.0]heptane-2-carboxylate | — |
| | (2S,5R,6R)-allyl 6-((R)-2-amino-2-phenylacetamido)-3,3-dimethyl-7-oxo-4-thia-1-azabicyclo[3.2.0]heptane-2-carboxylate | — |
| | (2S,5R,6R)-allyl 6-((R)-2-(allylamino)-2-phenylacetamido)-3,3-dimethyl-7-oxo-4-thia-1-azabicyclo[3.2.0]heptane-2-carboxylate) | — |

In a preferred embodiment of the present invention, R' and R" may be each independently hydrogen or a $C_{1-6}$ alkenyl group.

In a preferred embodiment of the present invention, $R_1$ may be hydrogen or a $C_{1-4}$ alkyl group.

In a preferred embodiment of the present invention, $R_2$ may be selected from the group consisting of a $C_{1-3}$ alkenyl group, a $C_{5-7}$ cycloalkyl group, a cyano group, a $C_{1-3}$ alkyl group, a $C_{6-8}$ aryl group, —$OR_3$ and —$COOR_4$.

In the present invention, the compound represented by formula 1 may preferably be one or more selected from the group consisting of (2S,5R,6R)-3,3-dimethyl-7-oxo-6-(2-phenylacetamido)-4-thia-1-azabicyclo[3.2.0]heptane-2-carboxylic acid; allyl (2S,5R,6R)-3,3-dimethyl-7-oxo-6-(2-phenylacetamido)-4-thia-1-azabicyclo[3.2.0]heptane-2-carboxylate; cyclohexylmethyl (2S,5R,6R)-3,3-dimethyl-7-oxo-6-(2-phenylacetamido)-4-thia-1-azabicyclo[3.2.0]heptane-2-carboxylate; 3-cyanopropyl (2S,5R,6R)-3,3-dimethyl-7-oxo-6-(2-phenylacetamido)-4-thia-1-azabicyclo[3.2.0]heptane-2-carboxylkate; and (2S,5R,6R)-6-((S)-2-amino-2-phenylacetamido)-3,3-dimethyl-7-oxo-4-thia-1-azabicyclo[3.2.0]heptane-2-carboxylic acid.

The present invention also provides a pharmaceutically acceptable salt of the compound represented by formula 1. The pharmaceutically acceptable salt should have low toxicity to the human body and should not affect the biological activity and physicochemical properties of its parent compound. The pharmaceutically acceptable salt may be an acid addition salt of the compound with a pharmaceutically acceptable free base, but is not limited thereto.

The preferred salt forms of the compound according to the present invention may be, for example, salts with inorganic acids such as hydrochloric acid, bromic acid, sulfuric acid, sodium hydrogen sulfate, phosphate, nitrate and carbonate; and salts with organic acids such as formic acid, acetic acid, propionic acid, oxalic acid, succinic acid, benzoic acid, citric acid, maleic acid, malonic acid, tartaric acid, gluconic acid, lactic acid, gentisic acid, fumaric acid, lactobionic acid, salicylic acid, trifluoroacetic acid and acetylsalicylic acid (aspirin); or salts with amino acids such as glycine, alanine, valine, isoleucine, serine, cysteine, cystine, aspartic acid, glutamine, lysine, arginine, tyrosine and proline; salts with sulfonic acids such as methanesulfonate, ethanesulfonate, benzenesulfonate and toluenesulfonate; metal salts formed by reaction with alkali metals such as sodium and potassium; or salts with ammonium ions, but are not limited thereto.

The salt can be prepared by a conventional method. For example, the salt can be prepared by dissolving the compound of formula 1 in a water-miscible solvent, such as methanol, ethanol, acetone or 1,4-dioxane, and then adding a free acid or a free base thereto, followed by crystallization.

In the present invention, a preferred example of the pharmaceutically acceptable salt of the compound represented by formula 1 may be one or more selected from among the salts shown in Table 2 below.

TABLE 2

| Structural formula | Compound name | Name |
|---|---|---|
| [structure of sodium salt with NH₂, phenyl, β-lactam, thiazolidine, ONa carboxylate] | Sodium (2S,5R,6R)-6-((R)-2-amino-2-phenylacetamido)-3,3-dimethyl-7-oxo-4-thia-1-azabicyclo[3.2.0]heptane-2-carboxylate | KRM-60036 |
| [structure of potassium salt with phenylacetamido, β-lactam, thiazolidine, O⁻ K⁺ carboxylate] | Potassium (2S,5R,6R)-3,3-dimethyl-7-oxo-6-(2-phenylacetamido)-4-thia-1-azabicyclo[3.2.0]heptane-2-carboxylate | KRM-60027 |

In addition, the hydrate form of the compound represented by formula 1 may also be included within the scope of the present invention.

In accordance with another embodiment of the present invention, there is provided a pharmaceutical composition for hardening soft tissue, comprising, as an active ingredient, the compound represented by formula 1 or a pharmaceutically acceptable salt or hydrate thereof.

In the present invention, the "soft tissue" may be one or more tissues selected from the group consisting of pancreas, liver, nerve, ligament, serosa, myofascia, intervertebral disc, and blood vessel, and may preferably be pancreas, but is not limited thereto.

The compound represented by formula 1 and a pharmaceutically acceptable salt and hydrate thereof, which are provided according to the present invention, can temporarily increase the hardness or tension of soft tissue, thereby increasing the efficiency of suturing during suturing of the soft tissue, thereby preventing sequela or the like from occurring due to insufficient anastomosis.

In accordance with still another embodiment of the present invention, there is provided a pharmaceutical composition for preventing pancreatic leakage, comprising, as an active ingredient, the compound represented by formula 1 or a pharmaceutically acceptable salt or hydrate thereof.

The compound represented by formula 1 and a pharmaceutically acceptable salt and hydrate thereof, which are provided according to the present invention, can temporarily increase the hardness or tension of the pancreas, thereby increasing the efficiency of suturing during pancreaticoduodenectomy and effectively preventing pancreatic leakage.

In accordance with still another embodiment of the present invention, the present invention is directed to a method for hardening soft tissue, comprising a step of administering to a subject an effective amount of the compound represented by formula 1 or a pharmaceutically acceptable salt or hydrate thereof.

In the present invention, the subject may be a subject requiring temporal hardening of soft tissue. More preferably, it may be a subject requiring surgical suturing of soft tissue.

In addition, in the present invention, the compound represented by formula 1 or a pharmaceutically acceptable salt or hydrate thereof may be administered to the soft tissue of the subject.

In the present invention, the "soft tissue" may be one or more tissues selected from the group consisting of pancreas, liver, nerve, ligament, serosa, myofascia, intervertebral disc, and blood vessel, and may preferably be pancreas, but is not limited thereto.

In accordance with still another embodiment of the present invention, the present invention is directed to a method for preventing pancreatic leakage, comprising a step of administering to a subject an effective amount of the compound represented by formula 1 or a pharmaceutically acceptable salt or hydrate thereof.

In the present invention, the subject may be a subject requiring pancreaticoduodenectomy.

In addition, in the present invention, the compound represented by formula 1 or a pharmaceutically acceptable salt or hydrate thereof may be administered to the pancreas of the subject.

The "effective amount" as used herein refers to an amount sufficient for achieving a temporal change in the hardness or tension of the soft tissue or pancreas of the subject.

In accordance with still another embodiment of the present invention, there is provided a pharmaceutical composition for hardening soft tissue, comprising, as an active ingredient, a compound selected from the group consisting of a hydroxyquinoline compound, a derivative thereof, and a pharmaceutically acceptable salt and hydrate thereof.

In the present invention, the hydroxyquinoline compound and a derivative thereof may be one or more selected from among the compounds shown in Table 3 below.

TABLE 3

| Structural formula | Compound name | Name |
|---|---|---|
| (7-chloro-4-hydroxyquinoline-3-carboxylic acid structure) | 7-chloro-4-hydroxy-3-quinolinecarboxylic acid | KRP-0001 |
| (5-chloro-8-hydroxyquinoline structure) | 5-chloro-8-hydroxyquinoline | KRP-0002 |
| (5-chloro-8-hydroxy-7-iodoquinoline structure) | 5-chloro-8-hydroxy-7-iodoquinoline | KRP-0003 |
| (5,7-diiodo-8-hydroxyquinoline structure) | 5,7-diiodo-8-hydroxyquinoline | KRP-0004 |
| (4,8-dihydroxyquinoline-2-carboxylic acid structure) | 4,8-dihydroxyquinoline-2-carboxylic acid | KRP-0005 |
| (4-hydroxy-2-methylquinoline structure) | 4-hydroxy-2-methylquinoline | KRP-0006 |
| (2-hydroxy-4-methylquinoline structure) | 2-hydroxy-4-methylquinoline | KRP-0007 |
| (8-hydroxy-5-nitroquinoline structure) | 8-hydroxy-5-nitroquinoline | KRP-0008 |

TABLE 3-continued

| Structural formula | Compound name | Name |
| --- | --- | --- |
| (4-hydroxy-7-trifluoromethyl-3-quinolinecarboxylic acid structure) | 4-hydroxy-7-trifluoromethyl-3-quinolinecarboxylic acid | KRP-0009 |
| (3-hydroxyisoquinoline structure) | 3-hydroxyisoquinoline | KRP-00010 |
| (4-hydroxy-7-methoxyquinoline structure) | 4-hydroxy-7-methoxyquinoline | KRP-00011 |
| (4-hydroxyquinoline structure) | 4-hydroxyquinoline | KRP-00012 |
| (6-hydroxyquinoline structure) | 6-hydroxyquinoline | KRP-00013 |
| (2-hydroxyquinoline structure) | 2-hydroxyquinoline | KRP-00014 |
| (7-hydroxyquinoline structure) | 7-hydroxyquinoline | KRP-00015 |
| (8-hydroxyquinoline-7-carboxylic acid structure) | 8-hydroxyquinoline-7-carboxylic acid | KRP-00016 |
| (8-hydroxy-5-quinoline sulfonic acid structure) | 8-hydroxy-5-quinoline sulfonic acid | — |
| (8-hydroxyquinoline structure) | 8-hydroxyquinoline | KRM-0042 |

In the present invention, the derivative of the hydroxyquinoline compound may preferably be one or more selected from the group consisting of 7-chloro-4-hydroxy-3-quinolinecarboxylic acid; 5-chloro-8-hydroxyquinoline; 5-chloro-8-hydroxy-7-iodoquinoline; 5,7-diiodo-8-hydroxyquinoline; 4,8-dihydroxyquinoline-2-carboxylic acid; 4-hydroxy-7-trifluoromethyl-3-quinolinecarboxylic acid; 3-hydroxyisoquinoline; 4-hydroxyquinoline; 6-hydroxyquinoline; 2-hydroxyquinoline; 8-hydroxyquinoline-7-carboxylic acid; and 8-hydroxyquinoline. More preferably, it may be 3-hydroxyisoquinoline.

The present invention also provides a pharmaceutically acceptable salt of the hydroxyquinoline compound or the derivative of the compound. The pharmaceutically acceptable salt should have low toxicity to the human body and should not affect the biological activity and physicochemical properties of its parent compound. The pharmaceutically acceptable salt may be an acid addition salt of the basic compound with a pharmaceutically acceptable free acid, but is not limited thereto.

The preferred salt forms of the compound according to the present invention may be, for example, salts with inorganic acids such as hydrochloric acid, bromic acid, sulfuric acid, sodium hydrogen sulfate, phosphate, nitrate and carbonate; and salts with organic acids such as formic acid, acetic acid, propionic acid, oxalic acid, succinic acid, benzoic acid, citric acid, maleic acid, malonic acid, tartaric acid, gluconic acid, lactic acid, gentisic acid, fumaric acid, lactobionic acid, salicylic acid, trifluoroacetic acid and acetylsalicylic acid (aspirin); or salts with amino acids such as glycine, alanine, valine, isoleucine, serine, cysteine, cystine, aspartic acid, glutamine, lysine, arginine, tyrosine and proline; salts with sulfonic acids such as methanesulfonate, ethanesulfonate, benzenesulfonate and toluenesulfonate; metal salts formed by reaction with alkali metals such as sodium and potassium; or salts with ammonium ions, but are not limited thereto.

The salt can be prepared by a conventional method. For example, the salt can be prepared by dissolving the hydroxyquinoline compound or the derivative of the compound in a water-miscible solvent, such as methanol, ethanol, acetone or 1,4-dioxane, and then adding a free acid or a free base thereto, followed by crystallization.

In addition, the hydrate form of the hydroxyquinoline compound or the derivative of the compound may also be included within the scope of the present invention. Preferably, the hydrate form may be a hydrate shown in Table 4 below, but is not limited thereto.

TABLE 4

| Structural formula | Compound name | Name |
|---|---|---|
| 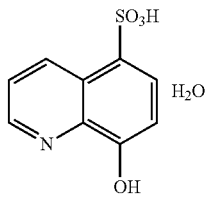 | 8-hydroxy-5-quinoline sulfonic acid hydrate | KRP-0017 |

In the present invention, the "soft tissue" may be one or more tissues selected from the group consisting of pancreas, liver, nerve, ligament, serosa, myofascia, intervertebral disc, and blood vessel, and may preferably be pancreas, but is not limited thereto.

The hydroxyquinoline compound, derivative thereof and pharmaceutically acceptable salt and hydrate thereof according to the present invention can temporarily increase the hardness or tension of soft tissue, thereby increasing the efficiency of suturing during suturing of the soft tissue, thereby preventing sequela or the like from occurring due to insufficient anastomosis.

In accordance with still another embodiment of the present invention, there is provided a pharmaceutical composition for preventing pancreatic leakage, comprising, as an active ingredient, a compound selected from the group consisting of the hydroxyquinoline compound, a derivative thereof, and a pharmaceutically acceptable salt and hydrate thereof.

In the present invention, the hydroxyquinoline compound and the derivative thereof may be one or more selected from among the compounds shown in Table 3 above.

In the present invention, the derivative of the hydroxyquinoline compound may preferably be one or more selected from the group consisting of 5-hydroxyquinoline; 7-chloro-4-hydroxy-3-quinolinecarboxylic acid; 5-chloro-8-hydroxyquinoline; 5-chloro-8-hydroxy-7-iodoquinoline; 5,7-diiodo-8-hydroxyquinoline; 4,8-dihydroxyquinoline-2-carboxylic acid; 4-hydroxy-7-trifluoromethyl-3-quinolinecarboxylic acid; 3-hydroxyisoquinoline; 4-hydroxyquinoline; 6-hydroxyquinoline; 2-hydroxyquinoline; 8-hydroxyquinoline-7-carboxylic acid; and 8-hydroxyquinoline. More preferably, it may be 3-hydroxyisoquinoline.

The present invention also provides a pharmaceutically acceptable salt of the hydroxyquinoline compound or the derivative of the compound. The pharmaceutically acceptable salt should have low toxicity to the human body and should not affect the biological activity and physicochemical properties of its parent compound. The pharmaceutically acceptable salt may be an acid addition salt of the basic compound with a pharmaceutically acceptable free acid, but is not limited thereto.

The preferred salt forms of the compound according to the present invention may be, for example, salts with inorganic acids such as hydrochloric acid, bromic acid, sulfuric acid, sodium hydrogen sulfate, phosphate, nitrate and carbonate; and salts with organic acids such as formic acid, acetic acid, propionic acid, oxalic acid, succinic acid, benzoic acid, citric acid, maleic acid, malonic acid, tartaric acid, gluconic acid, lactic acid, gentisic acid, fumaric acid, lactobionic acid, salicylic acid, trifluoroacetic acid and acetylsalicylic acid (aspirin); or salts with amino acids such as glycine, alanine, valine, isoleucine, serine, cysteine, cystine, aspartic acid, glutamine, lysine, arginine, tyrosine and proline; salts with sulfonic acids such as methanesulfonate, ethanesulfonate, benzenesulfonate and toluenesulfonate; metal salts formed by reaction with alkali metals such as sodium and potassium; or salts with ammonium ions, but are not limited thereto.

The salt can be prepared by a conventional method. For example, the salt can be prepared by dissolving the hydroxyquinoline compound or the derivative of the compound in a water-miscible solvent, such as methanol, ethanol, acetone or 1,4-dioxane, and then adding a free acid or a free base thereto, followed by crystallization.

In addition, the hydrate form of the hydroxyquinoline compound or the derivative of the compound may also be included within the scope of the present invention. Preferably, the hydrate form may be the hydrate shown in Table 4 above, but is not limited thereto.

The hydroxyquinoline compound, derivative thereof and pharmaceutically acceptable salt and hydrate thereof according to the present invention can temporarily increase the hardness or tension of the pancreas, thereby increasing the efficiency of suturing during pancreaticoduodenectomy and effectively preventing pancreatic leakage.

In accordance with still another embodiment of the present invention, the present invention is directed to a method for hardening soft tissue, comprising a step of administering to a subject an effective amount of a compound selected from the group consisting of the hydroxyquinoline compound, a derivative thereof, and a pharmaceutically acceptable salt and hydrate thereof.

In the present invention, the hydroxyquinoline compound, a derivative thereof, and a pharmaceutically acceptable salt and hydrate thereof are as described above with respect to the pharmaceutical composition for hardening soft tissue according to the present invention, and thus the detailed description thereof will be omitted herein.

In the present invention, the subject may be a subject requiring temporal hardening of soft tissue. More preferably, it may be a subject requiring surgical suturing of soft tissue.

In addition, in the present invention, the hydroxyquinoline compound, a derivative thereof, or a pharmaceutically acceptable salt or hydrate thereof may be administered to the soft tissue of the subject.

In the present invention, the "soft tissue" may be one or more tissues selected from the group consisting of pancreas, liver, nerve, ligament, serosa, myofascia, intervertebral disc, and blood vessel, and may preferably be pancreas, but is not limited thereto.

In accordance with still another embodiment of the present invention, the present invention is directed to a method for preventing pancreatic leakage, comprising a step of administering to a subject an effective amount of a compound selected from the group consisting of hydroxyquinoline compound, a derivative thereof, and a pharmaceutically acceptable salt and hydrate thereof.

In the present invention, the hydroxyquinoline compound, a derivative thereof, and a pharmaceutically acceptable salt and hydrate thereof are as described above with respect to the pharmaceutical composition for preventing pancreatic leakage according to the present invention, and thus the detailed description thereof will be omitted herein.

In the present invention, the subject may be a subject requiring pancreaticoduodenectomy.

In addition, in the present invention, the hydroxyquinoline compound, a derivative thereof, or a pharmaceutically acceptable salt or hydrate thereof may be administered to the pancreas of the subject.

In accordance with still another embodiment of the present invention, there is provided a pharmaceutical composition for hardening soft tissue, comprising, as an active ingredient, a compound represented by any one of the following formulas 2 to 9, or a pharmaceutically acceptable salt or hydrate thereof:

[Formula 2]

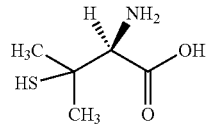

[Formula 3]

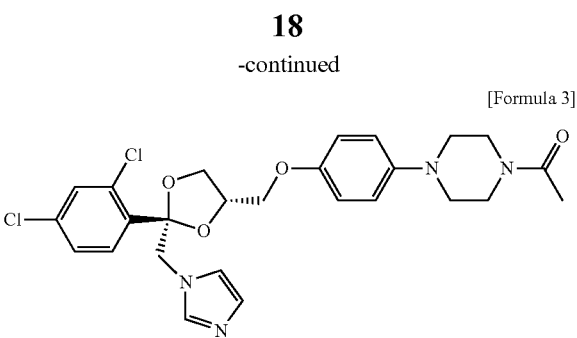

[Formula 4]

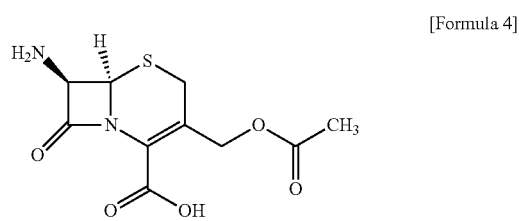

[Formula 5]

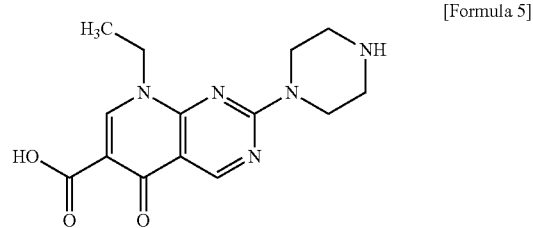

[Formula 6]

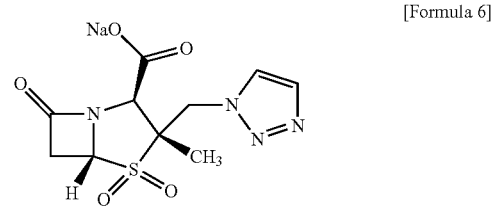

[Formula 7]

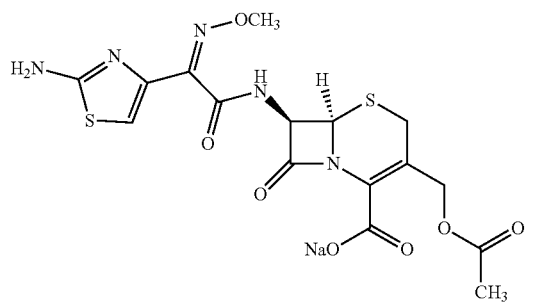

[Formula 8]

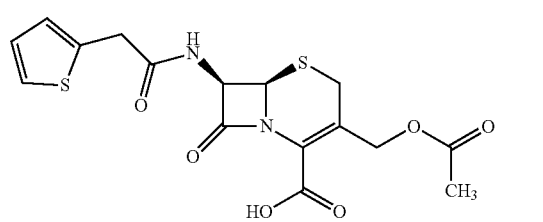

-continued

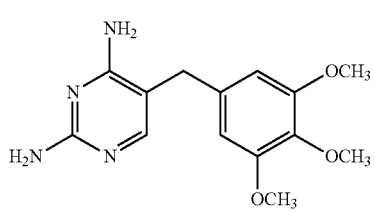

[Formula 9]

5

10

In the present invention, the detailed names of the compounds represented by formulas 2 to 9 are as shown in Table 5 below.

TABLE 5

| Structural formula | Compound name | Name |
| --- | --- | --- |
|  | (S)-2-amino-3-mercapto-3-methylbutanoic acid | KRM-60037 |
|  | 1-(4-(4-(((2R,4S)-2-((1H-imidazol-1-yl)methyl)-2-(2,4-dichlorophenyl)-1,3-dioxolan-4-yl)methoxy)phenyl)piperazin-1-yl)ethanone | KRM-60049 |
|  | (6R,7R)-3-(acetoxymethyl)-7-amino-8-oxo-5-thia-1-azabicyclo[4.2.0]oct-2-ene-2-carboxylic acid | KRM-60081 |
|  | 8-ethyl-5-oxo-2-(piperazin-1-yl)-5,8-dihydropyrido[2,3-d]pyrimidine-6-carboxylic acid | KRM-60082 |
|  | Sodium (2S,3S,5R)-3-((1H-1,2,3-triazol-1-yl)methyl)-3-methyl-7-oxo-4-thia-1-azabicyclo[3.2.0]heptane-2-carboxylate 4,4-dioxide | KRM-60084 |

TABLE 5-continued

| Structural formula | Compound name | Name |
|---|---|---|
| | Sodium (6R,7R)-3-(acetoxymethyl)-7-((Z)-2-(2-aminothiazol-4-yl)-2-(methoxyimino)acetamido)-8-oxo-5-thia-1-azabicyclo[4.2.0]oct-2-ene-2-carboxylate | KRM-60086 |
| | (6R,7R)-3-(acetoxymethyl)-8-oxo-7-(2-(thiophen-2-yl)acetamido)-5-thia-1-azabicyclo[4.2.0]oct-2-ene-2-carboxylic acid | — |
| | 5-(3,4,5-trimethoxybenzyl)pyrimidine-2,4-diamine | KRM-60088 |

The present invention also provides pharmaceutically acceptable salts of the compounds represented by formulas 2 to 9. The pharmaceutically acceptable salts should have low toxicity to the human body and should not affect the biological activities and physicochemical properties of their parent compounds. The pharmaceutically acceptable salts may be acid addition salts of the compounds of formulas 2 to 9 with pharmaceutically acceptable bases, but are not limited thereto.

The preferred salt forms of the compounds according to the present invention may be, for example, salts with inorganic acids such as hydrochloric acid, bromic acid, sulfuric acid, sodium hydrogen sulfate, phosphate, nitrate and carbonate; and salts with organic acids such as formic acid, acetic acid, propionic acid, oxalic acid, succinic acid, benzoic acid, citric acid, maleic acid, malonic acid, tartaric acid, gluconic acid, lactic acid, gentisic acid, fumaric acid, lactobionic acid, salicylic acid, trifluoroacetic acid and acetylsalicylic acid (aspirin); or salts with amino acids such as glycine, alanine, valine, isoleucine, serine, cysteine, cystine, aspartic acid, glutamine, lysine, arginine, tyrosine and proline; salts with sulfonic acids such as methanesulfonate, ethanesulfonate, benzenesulfonate and toluenesulfonate; metal salts formed by reaction with alkali metals such as sodium and potassium; or salts with ammonium ions, but are not limited thereto.

The salt can be prepared by a conventional method. For example, the salt can be prepared by dissolving the compound represented by any one of formulas 2 to 9 in a water-miscible solvent, such as methanol, ethanol, acetone or 1,4-dioxane, and then adding a free acid or a free base thereto, followed by crystallization.

In the present invention, a preferred example of a pharmaceutically acceptable salt of the compound represented by formula 8 may be the salt shown in Table 6 below.

TABLE 6

| Structural formula | Compound name | Name |
|---|---|---|
| | Sodium (6R,7R)-3-(acetoxymethyl)-8-oxo-7-(2-(thiophen-2-yl)acetamido)-5-thia-1-azabicyclo[4.2.0]oct-2-ene-2-carboxylate | KRM-60087 |

In addition, the hydrate forms of the compounds represented by formulas 2 to 9 may also be included within the scope of the present invention.

In the present invention, the "soft tissue" may be one or more tissues selected from the group consisting of pancreas, liver, nerve, ligament, serosa, myofascia, intervertebral disc, and blood vessel, and may preferably be pancreas, but is not limited thereto.

The compounds represented by formulas 2 to 9 and pharmaceutically acceptable salts and hydrates thereof according to the present invention can temporarily increase the hardness or tension of soft tissue, thereby increasing the efficiency of suturing during suturing of the soft tissue, thereby preventing sequela or the like from occurring due to insufficient anastomosis.

In accordance with still another embodiment of the present invention, there is provided a pharmaceutical composition for preventing pancreatic leakage, comprising, as an active ingredient, a compound represented by any one of the following formulas 2 to 9, or a pharmaceutically acceptable salt or hydrate thereof:

[Formula 2]

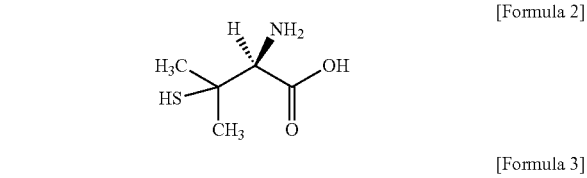

[Formula 3]

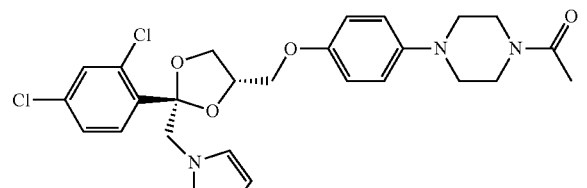

[Formula 4]

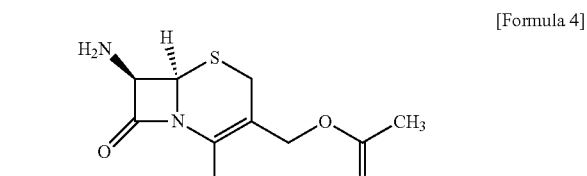

[Formula 5]

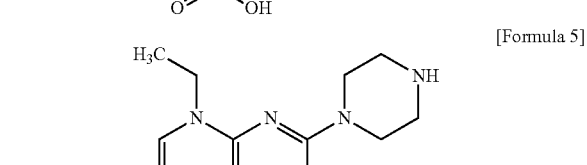

[Formula 6]

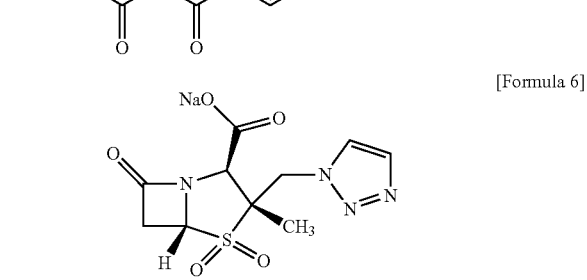

[Formula 7]

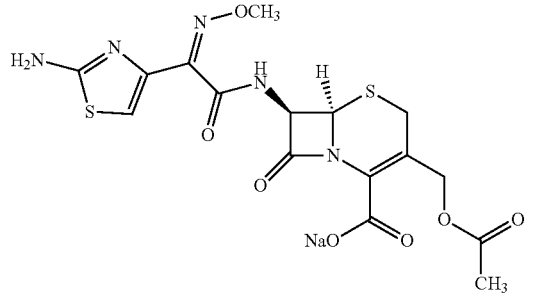

[Formula 8]

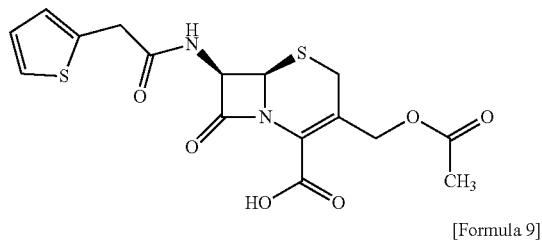

[Formula 9]

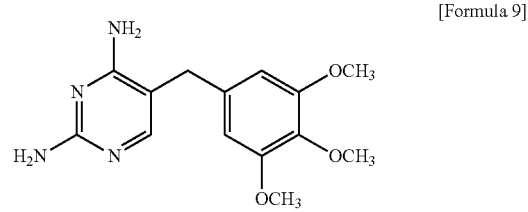

The present invention also provides pharmaceutically acceptable salts of the compounds represented by formulas 2 to 9. The pharmaceutically acceptable salts should have low toxicity to the human body and should not affect the biological activities and physicochemical properties of their parent compounds. The pharmaceutically acceptable salts may be acid addition salts of the compounds of formulas 2 to 9 with pharmaceutically acceptable free bases, but are not limited thereto.

The preferred salt forms of the compounds according to the present invention may be, for example, salts with inorganic acids such as hydrochloric acid, bromic acid, sulfuric acid, sodium hydrogen sulfate, phosphate, nitrate and carbonate; and salts with organic acids such as formic acid, acetic acid, propionic acid, oxalic acid, succinic acid, benzoic acid, citric acid, maleic acid, malonic acid, tartaric acid, gluconic acid, lactic acid, gentisic acid, fumaric acid, lactobionic acid, salicylic acid, trifluoroacetic acid and acetylsalicylic acid (aspirin); or salts with amino acids such as glycine, alanine, valine, isoleucine, serine, cysteine, cystine, aspartic acid, glutamine, lysine, arginine, tyrosine and proline; salts with sulfonic acids such as methanesulfonate, ethanesulfonate, benzenesulfonate and toluenesulfonate; metal salts formed by reaction with alkali metals such as sodium and potassium; or salts with ammonium ions, but are not limited thereto.

The salt can be prepared by a conventional method. For example, the salt can be prepared by dissolving the compound represented by any one of formulas 2 to 9 in a water-miscible solvent, such as methanol, ethanol, acetone or 1,4-dioxane, and then adding a free acid or a free base thereto, followed by crystallization.

In the present invention, a preferred example of a pharmaceutically acceptable salt of the compound represented by formula 8 may be the salt shown in Table 6 above.

In addition, the hydrate forms of the compounds represented by formulas 2 to 9 may also be included within the scope of the present invention.

The compounds represented by formulas 2 to 9 or pharmaceutically acceptable salts and hydrates thereof according to the present invention can temporarily increase the hardness or tension of pancreas, thereby increasing the efficiency of suturing during pancreaticoduodenectomy and effectively preventing pancreatic leakage.

In accordance with still another embodiment of the present invention, the present invention is directed to a method for hardening soft tissue, comprising a step of administering to a subject an effective amount of the compound represented by any one of formulas 2 to 9 or a pharmaceutically acceptable salt or hydrate thereof.

In the present invention, the compounds represented by formulas 2 to 9 and pharmaceutically acceptable salts and hydrates thereof are as described above with respect to the pharmaceutical composition for hardening soft tissue according to the present invention, and thus the detailed description thereof will be omitted herein.

In the present invention, the subject may be a subject requiring temporal hardening of soft tissue. More preferably, it may be a subject requiring surgical suturing of soft tissue.

In addition, in the present invention the compound represented by any one of formulas 2 to 9 or a pharmaceutically acceptable salt or hydrate thereof may be administered to the soft tissue of the subject.

In the present invention, the "soft tissue" may be one or more tissues selected from the group consisting of pancreas, liver, nerve, ligament, serosa, myofascia, intervertebral disc, and blood vessel, and may preferably be pancreas, but is not limited thereto.

In accordance with still another embodiment of the present invention, the present invention is directed to a method for preventing pancreatic leakage, comprising a step of administering to a subject an effective amount of the compound represented by any one of formulas 2 to 9 or a pharmaceutically acceptable salt or hydrate thereof.

In the present invention, the compounds represented by formulas 2 to 9 or pharmaceutically acceptable salts or hydrates thereof are as described above with respect to the pharmaceutical composition for preventing pancreatic leakage according to the present invention, and thus the detailed description thereof will be omitted herein.

In the present invention, the subject may be a subject requiring pancreaticoduodenectomy.

In addition, in the present invention, the compounds represented by formulas 2 to 9 or pharmaceutically acceptable salts or hydrates thereof may be administered to the pancreas of the subject.

In accordance with still another embodiment of the present invention, there is provided a method for preparing a compound derivative, comprising the steps of: dissolving a compound represented by the following formula 10 and 18-crown-6(1,4,7,10,13,16-hexaoxacyclooctadecane) in an organic solvent; and adding a compound represented by the following formula 11 to the dissolved solution, followed by stirring, thereby synthesizing a compound:

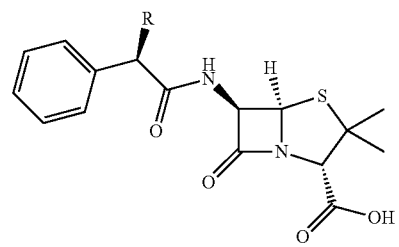 [SMILES: CC1(C)S[C@@H]2[C@H](NC(=O)[C@H](N)c3ccccc3)C(=O)N2[C@H]1C(=O)O]

[Formula 10]

$R_6$—Br    [Formula 11]

In formula 10 above,
R is hydrogen or N(R')(R''), and
R' and R'' are each independently hydrogen, a $C_{1-6}$ alkyl group or a $C_{1-6}$ alkenyl group, and
in formula 11 above,
$R_6$ is hydrogen or a $C_{1-6}$ alkyl group;
the $C_{1-6}$ alkyl group of $R_6$ is unsubstituted or substituted with $R_7$;
$R_7$ is selected from the group consisting of a $C_{1-6}$ alkenyl group, a $C_{3-7}$ cycloalkyl group, a cyano group, a $C_{1-6}$ alkyl group, a $C_{6-10}$ aryl group, —$OR_8$ and —$COOR_9$;
the aryl group of $R_7$ is unsubstituted or substituted with halogen;
$R_8$ is —$(CH_2)_nOR_{10}$;
n is an integer ranging from 0 to 3;
$R_9$ and $R_{10}$ are each independently $C_{1-6}$ alkyl.

In the present invention, the compound represented by formula 11 may be selected from the group consisting of 3-bromopropene, (bromomethyl)cyclohexane, 4-bromobutyronitrile, tert-butyl bromopropionate, 1-bromo-2-methylpropane, 2-fluorobenzyl bromide, and 2-(2-ethoxyethoxy) ethyl bromide, but is not limited as long as it is an alkyl bromide that may be substituted by reaction with the carboxylate of the formula.

In the present invention, the organic solvent is used to dissolve the compounds, and is preferably an aprotic polar solvent. Specifically, as the solvent, dioxane, tetrahydrofuran (THF), acetone, dimethyl sulfoxide (DMSO), dimethylformamide (DIVLF), 1-methyl-2-pyrrolidone (NMP) or the like may be used. More preferably, dimethylformamide (DMF) is used.

In accordance with still another embodiment of the present invention, there is provided a method for screening a compound for hardening the pancreas, the method comprising the steps of: (a) measuring the hardness or tension of the pancreas of a non-human mammal not treated with a candidate compound; (b) measuring the hardness or tension of the pancreas of a non-human mammal treated with the candidate compound; and (c) determining that when the hardness or tension of the pancreas, measured in step (b), is higher than the hardness or tension of the pancreas, measured in step (a), the compound is the compound for hardening the pancreas.

In the present invention, the KRM-60027 (penicillin G potassium salt) and KRM-60036 (ampicillin sodium salt) compounds are antibiotics having (R)-4-thia-1-azabicyclo [3,2,0]hepta-7-one as a skeleton, and belong to the same family. The two compounds differ in that KRM-60027 is a potassium salt and KRM-60036 is a sodium salt. In addition, KRM-60027 has a $CH_2$-bond at the benzylic position on the left side of the skeleton, whereas KRM-60036 has an amino acid substitution for one of hydrogen atoms present in the $CH_2$-bond at the benzylic position, which has the effect of increasing the pharmacokinetics (PK) of the drug. KRM-60027 showed the result of significantly increasing the tension of the pancreas, and KRM-60036 was found to significantly increase the hardness of the pancreas.

In the present invention, KRM-60037 (D-penicillamine) is a drug having a simple structure. It has a molecular weight of only 149, but exhibited the effect of increasing the tension by 1.5 times. In particular, this small molecule has advantages in that it has chemically modifiable moieties, and thus various substituents can be attached to the molecule, thereby sufficiently increasing the tension and hardness of the pancreas.

In the present invention, KRM-60042 (8-hydroxyquinoline) is also a low-molecular-weight compound having a simple skeleton and a molecular weight of 145, and various substituents can be easily attached thereto. It can be seen that KRM-60042 significantly increases both the hardness and tension of the pancreas.

In the present invention, KRM-60049 (ketoconazole) has advantages in that it has an ideal molecular weight of 530 and contains many functional groups capable of forming salts such as piperazine and imidazole salts, thus making various salts.

In the present invention, the "hardness" means the level of resistance to the strain of particularly soft tissue, preferably the pancreas, among human organs, when an external force is applied to the outside of the pancreas. The measurement of the hardness according to the present invention is performed using a hardness meter, and measurement of the hardness of the pancreas is performed by measuring elastic modulus (EM) based on the Hooke's law and the Hertz's contact stress theory. The EM is a measure of the stiffness of an elastic material, and is expressed as the ratio of "the stress along the axis" and "the total strain along the axis within the range of the stress" by the Hooke's law.

In the present invention, the "tension" means a force which occurs in particularly soft tissue, preferably the pancreas, among human organs. Specifically, it means a force which occurs in an organ in response to an external force exerted by stretching or pulling action. The measurement of the tension according to the present invention is performed using a dynamometer. More specifically, the tension is determined by measuring suture-holding capacity using a Newton dynamometer. At this time, the tension is calculated by adding the weight of the tissue.

In one embodiment of the present invention, the "alkyl" means saturated straight or branched chain hydrocarbon groups, for example, methyl, ethyl, propyl, butyl, isobutyl, tert-butyl, and pentyl. As used herein, the "$C_{1-6}$ alkyl group" means an alkyl group containing 1 to 6 carbon atoms.

In one embodiment of the present invention, the "cycloalkyl" means a monocyclic or polycyclic saturated ring containing carbon and hydrogen atoms.

In one embodiment of the present invention, the "aryl" means a fully or partially unsaturated monocyclic or polycyclic carbon ring having aromaticity. The aryl group of the present invention is preferably monocryl or biaryl.

In one embodiment of the present invention, the "alkenyl" means an alkyl radical having one or more carbon-carbon double bonds. Here, the alkyl is as defined above.

In one embodiment of the present invention, the "halogen" or "halo" means fluorine, chlorine, bromine or iodine, unless otherwise indicated.

The pharmaceutical composition of the present invention comprises a pharmaceutically acceptable carrier in addition to the active ingredient compound. The pharmaceutically acceptable carrier that is contained in the pharmaceutical composition of the present invention is one that is generally used in drug formulations, and examples thereof include, but are not limited to, lactose, dextrose, sucrose, sorbitol, mannitol, starch, acacia rubber, potassium phosphate, alginate, gelatin, potassium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil.

The pharmaceutical composition according to the present invention may further comprise lubricants, wetting agents, sweeteners, flavoring agents, emulsifiers, suspending agents, and preservatives. Details of suitable pharmaceutically acceptable carriers and formulations can be found in Remington's Pharmaceutical Sciences ($19^{th}$ edition, 1995).

The pharmaceutical composition according to the present invention may be administered orally or parenterally, preferably parenterally. Parenteral administration may be performed by intravenous injection, subcutaneous injection, intramuscular injection, intraperitoneal injection, transdermal administration or intra-articular injection. More specifically, it is performed by intramuscular injection or intraperitoneal injection.

The suitable dose of the pharmaceutical composition of the present invention may vary depending on the drug formulation method, the mode of administration, the patient's age, body weight, sex, disease condition, diet, the period of administration, the route of administration, the rate of excretion, and sensitivity to the pharmaceutical composition used. Preferably, the pharmaceutical composition of the present invention may be administered at a daily dose of 0.001 to 10000 mg/kg (body weight).

According to conventional techniques known to those skilled in the art, the pharmaceutical composition according to the present invention is formulated with a pharmaceutically acceptable carrier and/or vehicle as described above, finally providing several forms including a unit dose form and a multi-dose form. Non-limiting examples of the formulations include, but not limited to, a solution, a suspension or an emulsion in oil or aqueous medium, an elixir, a powder, a granule, a tablet and a capsule, and may further comprise a dispersion agent or a stabilizer.

Advantageous Effects

The compounds according to the present invention can temporarily increase the hardness or tension of soft tissue, thereby increasing the efficiency of suturing during suturing of the soft tissue, thereby preventing sequela or the like from occurring due to insufficient anastomosis.

In addition, the compounds according to the present invention can temporarily increase the hardness or tension of soft tissue, particularly the pancreas, thereby increasing the efficiency of suturing during pancreaticoduodenectomy and effectively preventing pancreatic leakage.

DESCRIPTION OF DRAWINGS

FIG. 1 graphically shows the changes in the hardness of the mouse pancreas after treatment of the pancreas with the antibiotics KRM-60027, KRM-60036, KRM-60037, KRM-60042 and KRM-60049 according to the present invention in one example of the present invention.

FIG. 2 graphically shows the changes in the tension of the mouse pancreas after treatment of the pancreas with the antibiotics KRM-60027, KRM-60036, KRM-60037, KRM-60042 and KRM-60049 according to the present invention in one example of the present invention;

FIG. 3 graphically shows the changes in the hardness of the mouse pancreas after treatment of the pancreas with the antibiotics KRM-60028, KRM-60029 and KRM-60030 according to the present invention in one example of the present invention.

FIG. 4 graphically shows the changes in the tension of the mouse pancreas after treatment of the pancreas with the antibiotics KRM-60028, KRM-60029 and KRM-60030 according to the present invention in one example of the present invention.

FIG. 5 graphically shows the changes in the hardness of the mouse pancreas after treatment of the pancreas with the antibiotics ICRP-00001 to KRP-000017 according to the present invention in one example of the present invention.

FIG. 6 graphically shows the changes in the tension of the mouse pancreas after treatment of the pancreas with the antibiotics KRP-00001 to KRP-00017 according to the present invention in one example of the present invention.

FIG. 7 graphically shows the changes in the hardness of the mouse pancreas after treatment of the pancreas with the antibiotics KRM-60077 to KRM-60088 according to the present invention in one example of the present invention.

FIG. 8 graphically shows the changes in the tension of the mouse pancreas after treatment of the pancreas with the antibiotics KRM-60077 to KRM-60088 according to the present invention in one example of the present invention.

BEST MODE

In accordance with one embodiment of the present invention, there is provided a compound represented by the following formula 1 or a pharmaceutically acceptable salt or hydrate thereof:

[Formula 1]

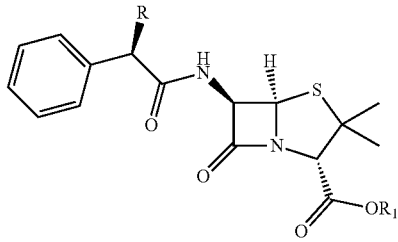

wherein
R is hydrogen or N(R')(R");
R' and R" are each independently hydrogen, a $C_{1-6}$ alkyl group or a $C_{1-6}$ alkenyl group;
$R_1$ is hydrogen or a $C_{1-6}$ alkyl group;
the $C_{1-6}$ alkyl group of $R_1$ is unsubstituted or substituted with $R_2$;
$R_2$ is selected from the group consisting of a $C_{1-6}$ alkenyl group, a $C_{3-7}$ cycloalkyl group, a cyano group, a $C_{1-6}$ alkyl group, a $C_{6-10}$ aryl group, —$OR_3$ and —$COOR_4$;
the aryl group of $R_2$ is unsubstituted or substituted with halogen;
$R_3$ is —$(CH_2)_mOR_5$;
m is an integer ranging from 0 to 3; and
$R_4$ and $R_5$ are each independently a $C_{1-6}$ alkyl group.

In accordance with another embodiment of the present invention, there is provided a pharmaceutical composition for hardening soft tissue, comprising, as an active ingredient, the compound represented by formula 1 or a pharmaceutically acceptable salt or hydrate thereof.

In accordance with still another embodiment of the present invention, there is provided a pharmaceutical composition for hardening soft tissue, comprising, as an active ingredient, a compound selected from the group consisting of a hydroxyquinoline compound, a derivative thereof, and a pharmaceutically acceptable salt and hydrate thereof.

In accordance with still another embodiment of the present invention, there is provided a pharmaceutical composition for hardening soft tissue, comprising, as an active ingredient, a compound represented by any one of the following formulas 2 to 9 or a pharmaceutically acceptable salt or hydrate thereof:

[Formula 2]

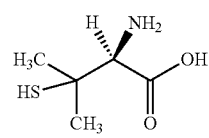

[Formula 3]

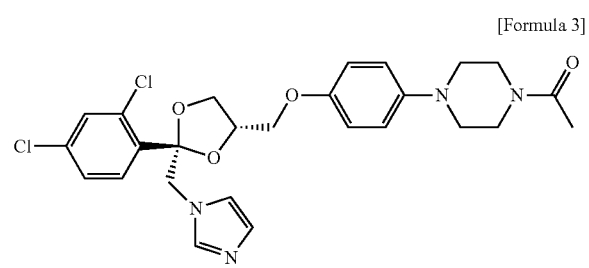

[Formula 4]

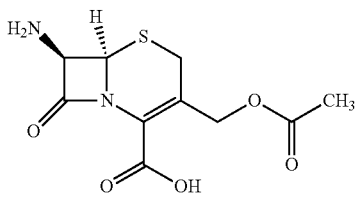

[Formula 5]

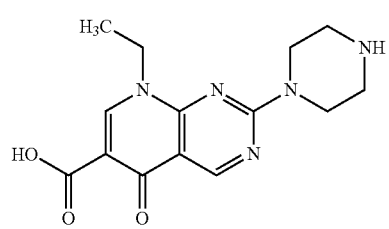

[Formula 6]

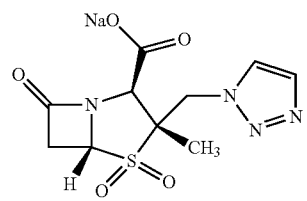

-continued

[Formula 7]

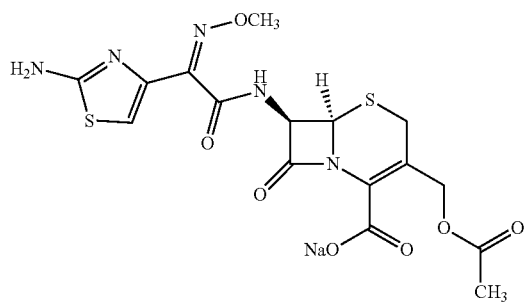

[Formula 8]

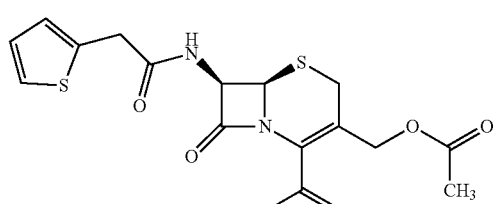

[Formula 9]

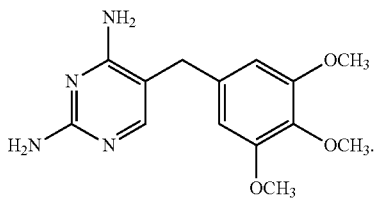

MODE FOR INVENTION

Hereinafter, the present invention will be described in detail with reference to examples. It will be obvious to those skilled in the art that these examples are only intended to illustrate the present invention in more detail and that the scope of the present invention as defined by the appended claims is not limited by these examples.

Example 1

Selection of Starting Compounds for Synthesis of Compounds for Hardening Pancreas To select starting compounds for synthesizing compounds that can enhance the function of the pancreas, a total of 23 antibiotics as shown below were prepared:

KRM-60027

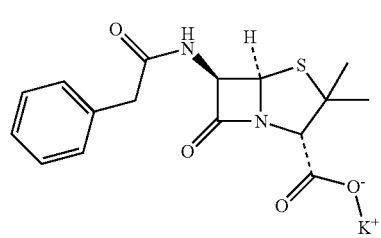

Penicilin G potassium salt

KRM-60036

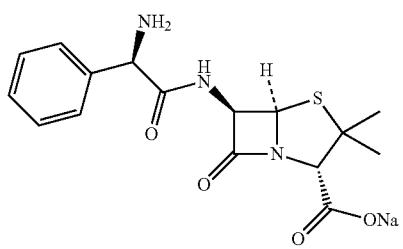

Ampicillin sodium salt

KRM-60037

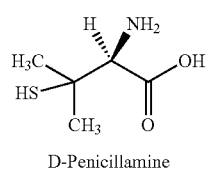

D-Penicillamine

KRM-60038

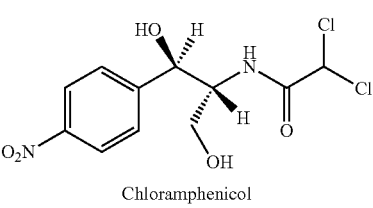

Chloramphenicol

KRM-60039

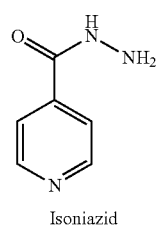

Isoniazid

KRM-60040

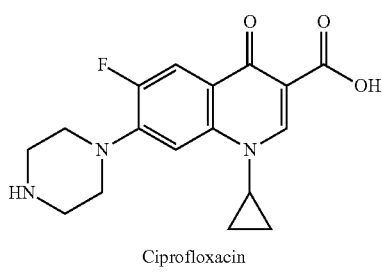

Ciprofloxacin

-continued
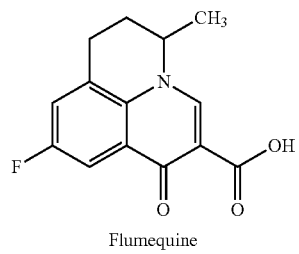
Flumequine
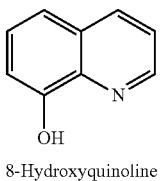
KRM-60041
8-Hydroxyquinoline
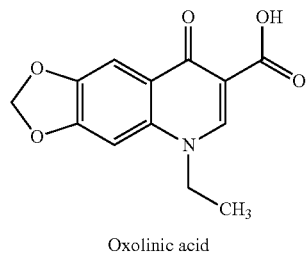
Oxolinic acid
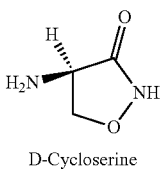
KRM-60043
D-Cycloserine
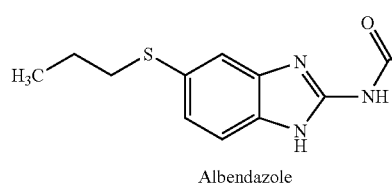
Albendazole
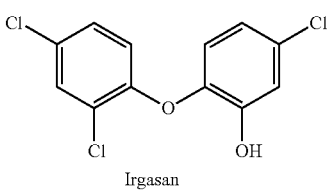
KRM-60045
Irgasan
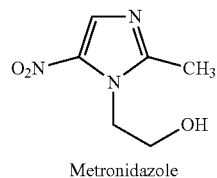
Metronidazole
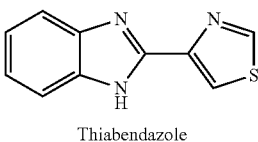
KRM-60047
Thiabendazole
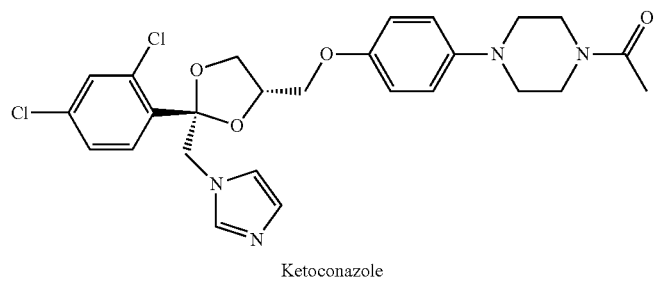
Ketoconazole
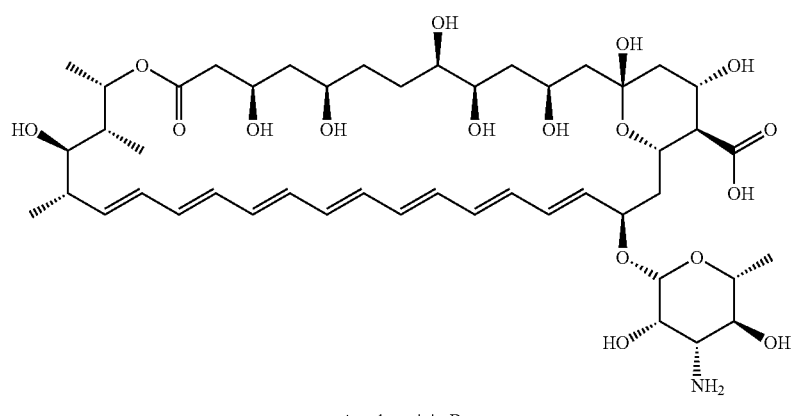
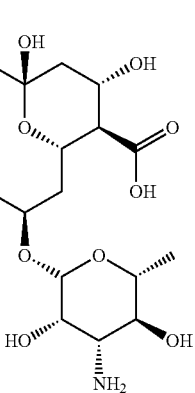
Amphotericin B
KRM-60042
KRM-60044
KRM-60046
KRM-60048
KRM-60049
KRM-60050

-continued
KRM-60051
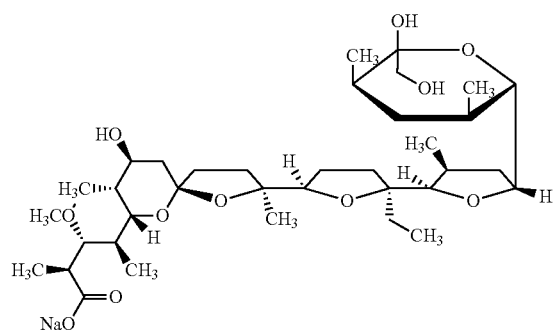
Monensin sodium salt
KRM-60052
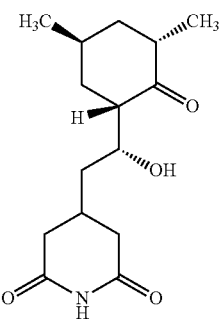
Cycloheximide
KRM-60053
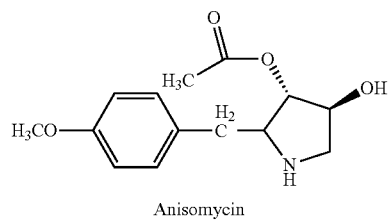
Anisomycin
KRM-60054
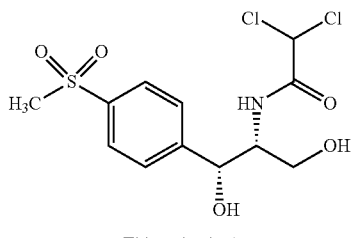
Thiamphenicol
KRM-60056
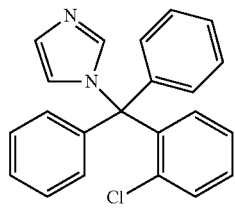
Clotrimazole
KRM-60054
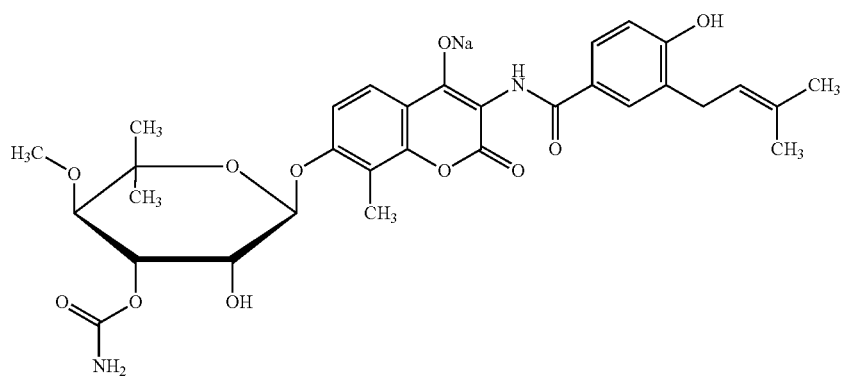
Novobiocin sodium salt
KRM-60057
cefazolin sodium salt More specifically, three mice were treated with 1 mM of each of the antibiotics shown above, and three mice were treated with phosphate buffered saline (PBS) as a control. Furthermore, the tension and hardness of the pancreases of the mice treated with each antibiotic were compared with those of the pancreases of the control mice not treated with the antibiotic, and antibiotics showing increased tension and hardness upon treatment were selected as starting compounds.

As a result, it was confirmed that among the 23 compounds, only KRM-60027, KRM-60036, KRM-60037, KRM-60042 and KRM-60049 compounds had the effects of increasing the tension and hardness of the pancreas. FIGS. 1 and 2 graphically show the changes in the hardness and tension of the pancreas after treatment with these five compounds compared to the control. Here, the hardness and the tension were measured using the methods described below.

(1) Measurement of Hardness

In order to measure the resistance of the pancreas using a hardness meter, the elastic modulus (EM) of the dissected pancreas was measured using Venustron (Axiom, Koriyama, Japan) based on the Hooke's law and the Hertz's contract stress theory, and the resistance of the pancreas was calculated using the following equation:

$$E = \frac{3}{4} \cdot F \cdot (1-v^2) \cdot t^{-\frac{3}{2}} \cdot R^{-\frac{1}{2}}.$$

(F, force; v, Poisson's ratio; t, variant of compression; r, the diameter of a rigid spherical probe that presses an object vertically)

(2) Measurement of Tensile

The tension of the pancreas was measured using a dynamometer. Specifically, a pancreatic fragment having a size of 1×1×1.5 cm was prepared, and then silk 4-0 suture was passed through the tissue to form a knob, and suture-holding capacity was measured using a Newton dynamometer. At this time, the tension was calculated by adding the weight of the tissue.

As shown in FIGS. 1 and 2, it could be seen that the pancreas of the mice was treated with each of the five antibiotics according to the present invention, that is, KRM-60027 (penicillin G potassium salt), KRM-60036 (ampicillin sodium salt), KRM-60037 (D-penicillamine), KRM-60042 (8-hydroxyquinoline) and KRM-60049 (ketoconazole), the tension and/or hardness of the pancreas significantly increased compared to the control. More specifically, it could be seen that KRM-60027 increased the tension of the pancreas to a significant level, and KRM-60036 significantly increased the hardness of the pancreas. In addition, it could be seen that KRM-60037, a drug having a simple structure and a molecular weight of only 149, exhibited the effect of increasing the tension of the pancreas by 1.5 times, and KRM-60042 and KRM-60049 increased both the hardness and tension of the pancreas to high levels.

Based on these results, the five antibiotics were selected as starting compounds for compounds capable of hardening the pancreas.

Synthetic Example 1

Synthesis of Derivatives of KRM-60027

The KRM-60027 compound which showed an excellent effect on an increase in the tension of the pancreas in Example 1 above was used as a starting material. Various alkyl bromide compounds were bound at the carboxylate position of KRM-60027, thereby synthesizing final compounds for enhancing the function of the pancreas.

Synthetic Example 1-1

Synthesis of KRM-60028

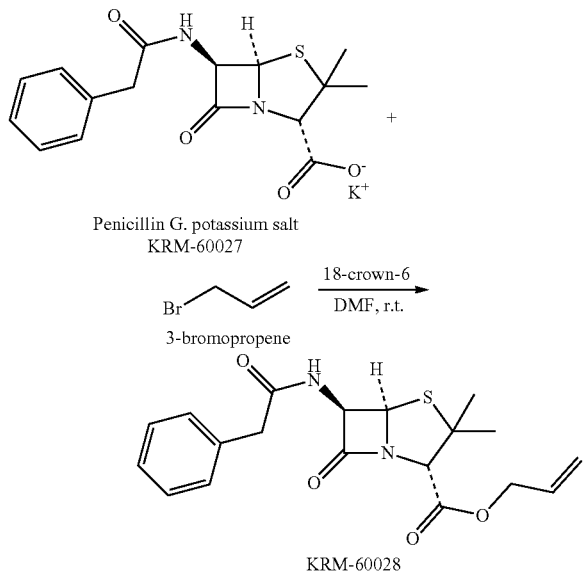

The KRM-60027 compound used as a starting material and 18-crown-6 (1,4,7,10,13,16-hexaoxacyclooctadecane) were dissolved in DMF (dimethylformamide), and then 3-bromopropene as alkyl bromide was added thereto, followed by stirring at room temperature for 24 hours. After completion of the reaction was confirmed by thin-layer chromatography (TLC), ethyl acetate was added to the reaction solution which was then washed several times with water. The ethyl acetate layer containing the product was separated, and then anhydrous sodium sulfate was added thereto to remove the remaining water, followed by concentration. The concentrate was purified by column chromatography, thereby obtaining the final product (KRM-60028) in which the carboxylate of KRM-60027 was substituted with allyl.

Synthetic Example 1-2

Synthesis of KRM-60029

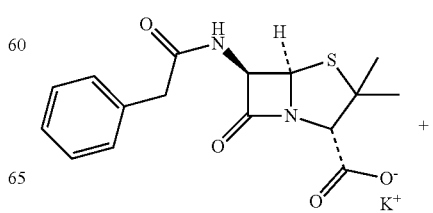

-continued

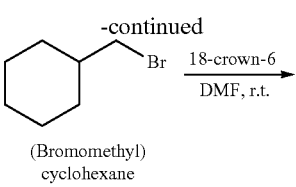

(Bromomethyl)
cyclohexane

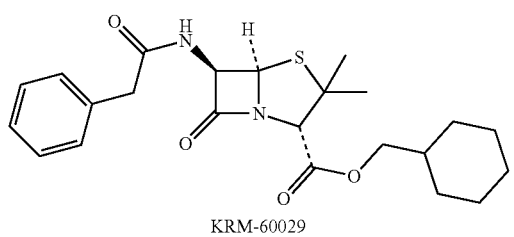

KRM-60029

A final product in which the carboxylate of KRM-60027 was substituted with cyclohexyl was obtained in the same manner as described in Synthetic Example 1-1, except that 4-(bromomethyl)cyclohexane was used instead of 3-bromopropene as the alkyl bromide.

Synthetic Example 1-3

Synthesis of KRM-60030

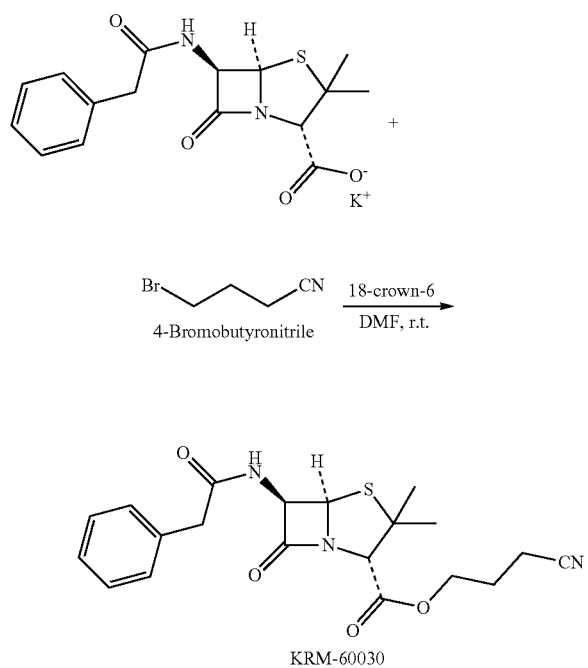

KRM-60030

A final product in which the carboxylate of KRM-60027 was substituted with cyanobutyl was obtained in the same manner as described in Synthetic Example 1-1, except that 4-bromobutyronitrile was used instead of 3-bromopropene as the alkyl bromide.

Synthetic Example 1-4

Synthesis of KRM-60077

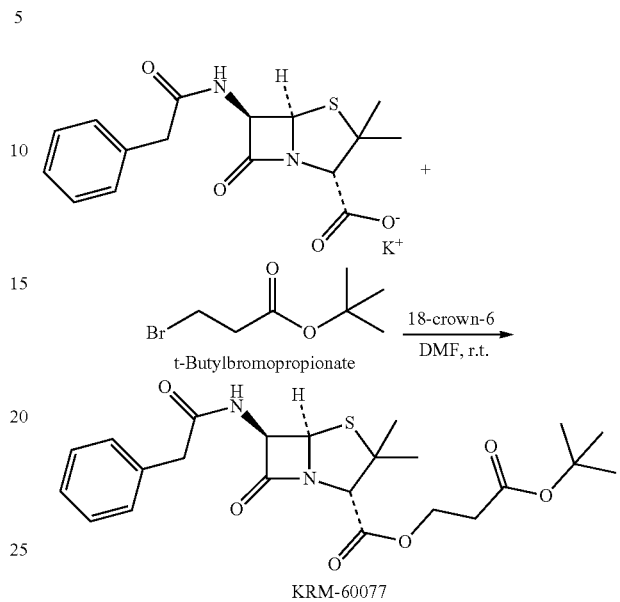

KRM-60077

A final product in which the carboxylate of KRM-60027 was substituted with tert-butyl propionate was obtained in the same manner as described in Synthetic Example 1-1, except that tert-butyl bromopropionate was used instead of 3-bromopropene as the alkyl bromide.

Synthetic Example 1-5

Synthesis of KRM-60078

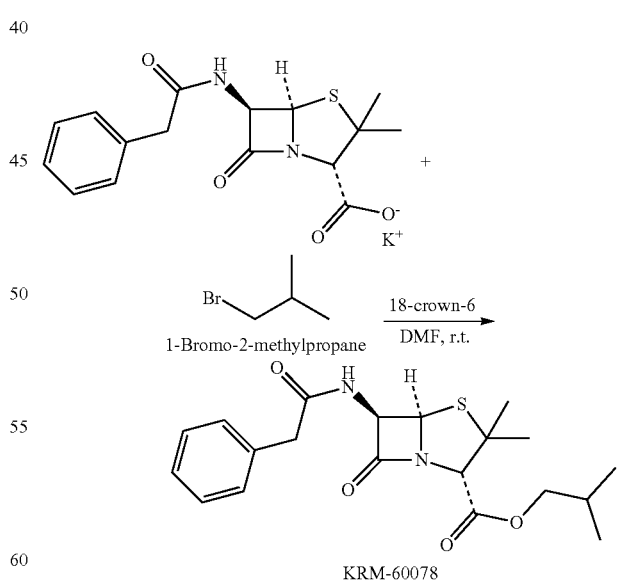

KRM-60078

A final product in which the carboxylate of KRM-60027 was substituted with isobutyl was obtained in the same manner as described in Synthetic Example 1-1, except that 1-bromo-2-methylpropane was used instead of 3-bromopropene as the alkyl bromide.

Synthetic Example 1-6

Synthesis of KRM-60079

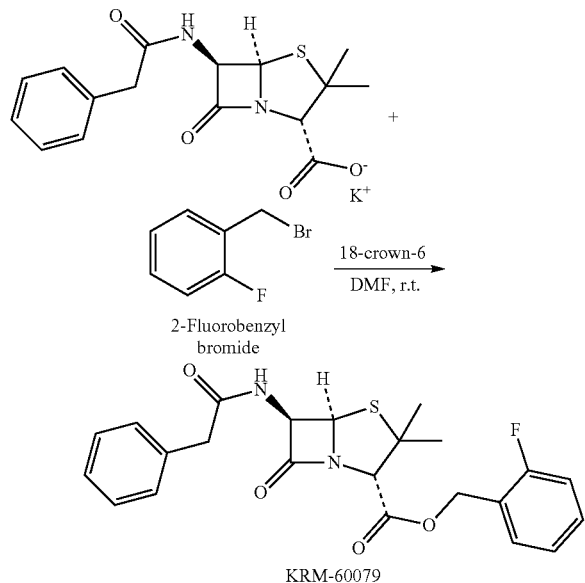

KRM-60079

A final product in which the carboxylate of KRM-60027 was substituted with 2-fluorobenzyl was obtained in the same manner as described in Synthetic Example 1-1, except that 2-fluorobenzyl bromide was used instead of 3-bromopropene as the alkyl bromide.

Synthetic Example 1-7

Synthesis of KRM-60080

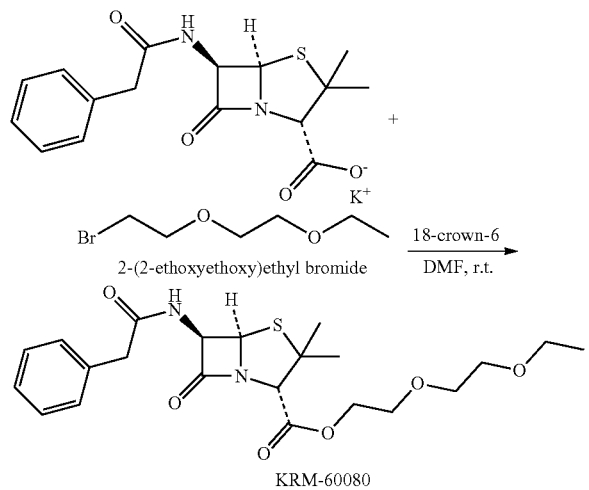

KRM-60080

A final product in which the carboxylate of KRM-60027 was substituted with ethylene glycol was obtained in the same manner as described in Synthetic Example 1-1, except that 2-(2-ethoxyethoxy)ethyl bromide was used instead of 3-bromopropene as the alkyl bromide.

Example 2

Additional Selection of Compounds for Hardening Pancreas

The pancreas of mice was treated with each of KRM-60028, KRM-60029 and KRM-60030 (synthesized in Synthetic Example 1 above) in the same manner as described in Example 1 above, and then changes in the hardness and tension of the pancreas compared to those of an untreated control group were measured. The results of the measurement are graphically shown in FIGS. 3 and 4.

As shown in FIGS. 3 and 4, it could be confirmed that when the pancreas of mice was treated with each of KRM-60028, KRM-60029 and KRM-60030 according to the present invention, both the hardness and tension of the pancreas increased compared to those of the control. Referring to Example 1, the starting compound KRM-60027 showed an insignificant change in the hardness of the pancreas and a significant increase in the tension of the pancreas, compared to the control. It could be seen that KRM-60028, KRM-60029 and KRM-60030, which are compounds modified from KRM-60027, increased both the hardness and tension of the pancreas. In particular, the KRM-60030 compound is a derivative obtained by attaching a cyanopropyl group to the carboxylate group of KRM-60027, and has a nitrile group at the right end portion, and thus has a functional group capable of functioning as a hydrogen bonding acceptor. It could be seen that this KRM-60030 compound increase the hardness of the pancreas by 1.5 times and the tension of the pancreas by 2 times, compared to those of the control.

This suggests that the compound represented by formula 1 according to the present invention can increase the hardness and tension of the pancreas, thereby temporarily hardening the pancreas.

Synthetic Example 2

Synthesis of Derivatives of KRM-60036

The KRM-60036 compound which showed an excellent effect on an increase in the hardness of the pancreas in Example 1 above was used as a starting material. Alkyl bromide compounds were introduced selectively at the carboxylate position of KRM-60036 while maintaining the amine of KRM-60036, thereby synthesizing final compounds for enhancing the function of the pancreas. Specifically, as shown in reaction scheme 1 below, the amine of the KRM-60036 compound used as a starting material was subjected to boc protection. Then, as shown in reaction scheme 2 below, using 3-bromopropene, (bromomethyl)cyclohexane and 4-bromobutyronitrile as alkyl bromides, an alkyl group was introduced in the same manner as described in Synthetic Example 1-1 above, followed by boc deprotection, thereby obtaining final amine compounds.

<Reaction Scheme 1>
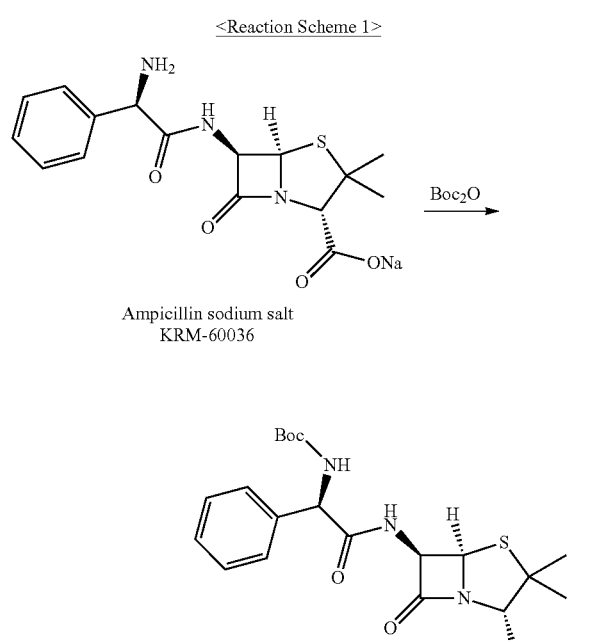
Reaction Scheme 2
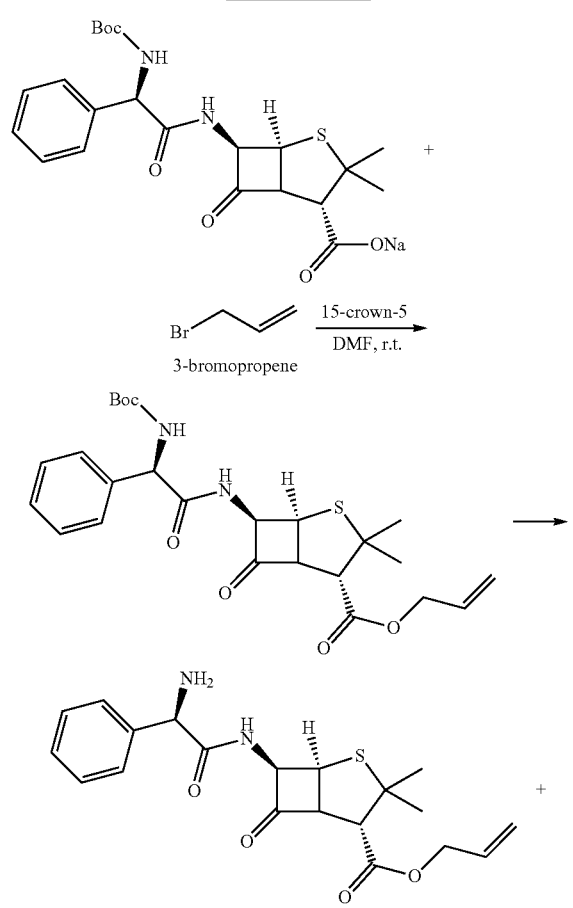
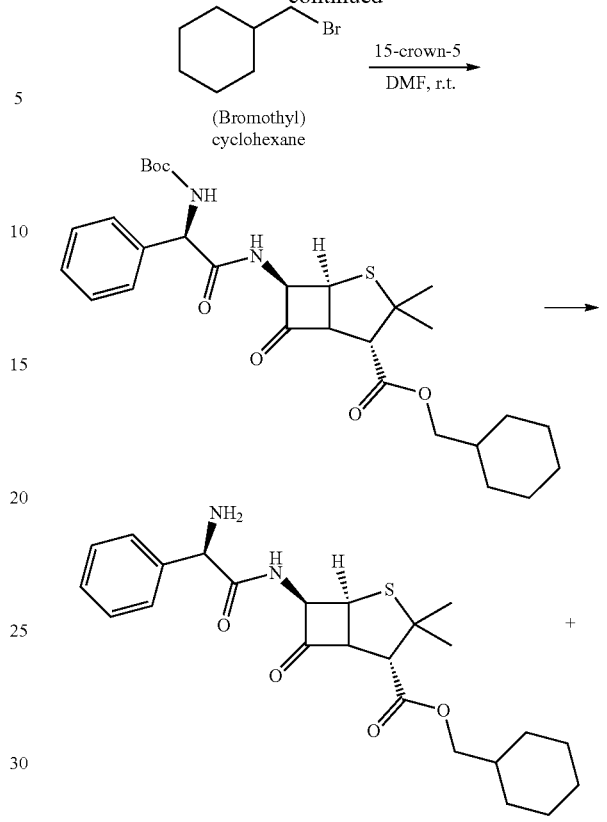
Example 3
Derivatives of KRM-60042
The following derivative compounds were prepared, which are based on a hydroxyl group and quinoline which are the basic skeleton of the KRM-60042 compound (Sigma-Aldrich, cat. No 252565 148-24-3) which showed excellent effects on increases in both the hardness and tension of the pancreas in Example 1 above.

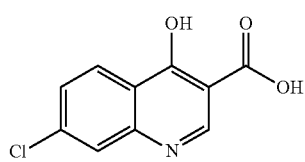 [SMILES: O=C(O)c1cnc2cc(Cl)ccc2c1O]
7-chloro-4-hydroxy-3-quinolinecarboxylic acid
KRP-00001

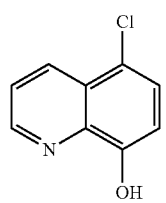
5-chloro-8-hydroxyquinoline
KRP-00002

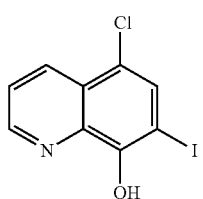 [SMILES: Oc1c(I)cc(Cl)c2cccnc12]
5-chloro-8-hydroxy-7-iodoquinoline
KRP-00003

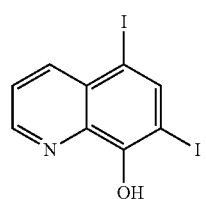
5,7-diiodo-8-hydroxyquinoline
KRP-00004

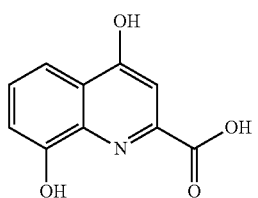 [SMILES: O=C(O)c1cc(O)c2cccc(O)c2n1]
4,8-dihydroxyquinoline-2-carboxylic acid
KRP-00005

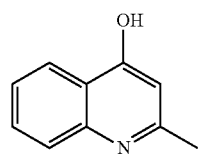
4-hydroxy-2-methylquinoline
KRP-00006

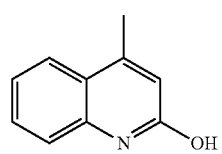
2-hydroxy-4-methylquinoline
KRP-00007

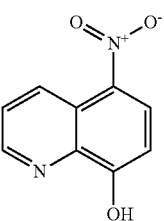
8-hydroxy-5-nitroquinoline
KRP-00008

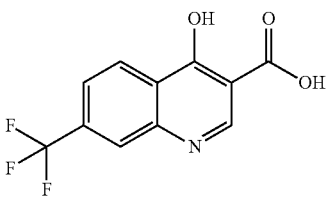 [SMILES: O=C(O)c1cnc2cc(C(F)(F)F)ccc2c1O]
4-hydroxy-7-trifluoromethyl-3-quinolinecarboxylic acid
KRP-00009

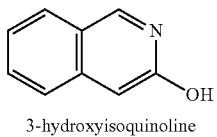
3-hydroxyisoquinoline
KRP-00010

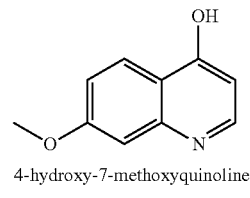
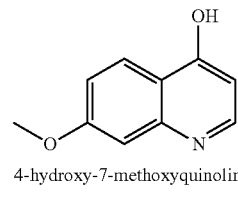
4-hydroxy-7-methoxyquinoline
KRP-00011

4-hydroxyquinoline
KRP-00012

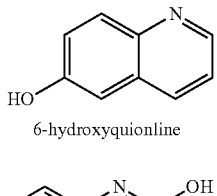
6-hydroxyquionline
KRP-00013

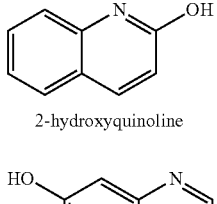
2-hydroxyquinoline
KRP-00014

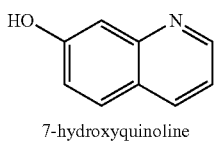
7-hydroxyquinoline
KRP-00015

-continued

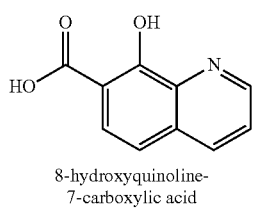

KRP-00016

8-hydroxyquinoline-
7-carboxylic acid

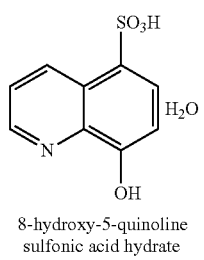

KRP-00017

8-hydroxy-5-quinoline
sulfonic acid hydrate

The pancreas of mice was treated with each of KRP-0001 to KRP-00017 (a total of 17 compounds) in the same manner as described in Example 1 above, and then the changes in the hardness and tension of the pancreas compared to those of an untreated control group were measured. The results of the measurement are graphically shown in FIGS. 5 and 6.

As shown in FIGS. 5 and 6, it could be confirmed that among the 17 derivatives having the quinoline of KRM-60042 as a skeleton, treatment with 11 compounds (KRP-00001, KRP-00002, KRP-00003, KRP-00004, KRP-00005, KRP-00006, KRP-00009, KRP-00012, KRP-00013, KRP-00014 and KRP-00016) increased both the hardness and tension of the pancreas, and particularly, treatment with 10 compounds (ICRP-00001, KRP-00002, KRP-00003, KRP-00004, KRP-00005, KRP-00009, KRP-00012, KRP-00013, KRP-00014 and KRP-00016) increased the tension by at least 1.5 times, and treatment with KRP-00010 increased the tension by about 2.4 times, compared to that of the control group.

This suggests that the hydroxyquinoline derivatives according to the present invention exhibited the effect of significantly increasing the tension of the pancreas and also increased the hardness of the pancreas.

Example 4

Other Compounds

The pancreas of mice was treated with each of KRM-60077 to KRM-60080 (synthesized in Synthetic Example 1) and KRM-60081 to KRM-60088 compounds (shown below) in the same manner as described in Example 1 above, and then the changes in the hardness and tension of the pancreas compared to those of an untreated control group were measured. The results of the measurement are graphically shown in FIGS. 7 and 8.

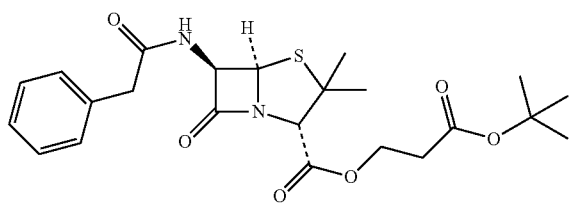

KRM-60077

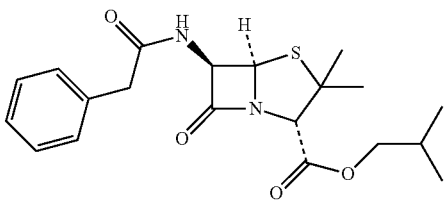

KRM-60078

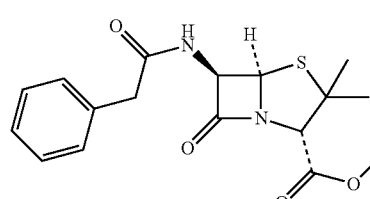

KRM-60079

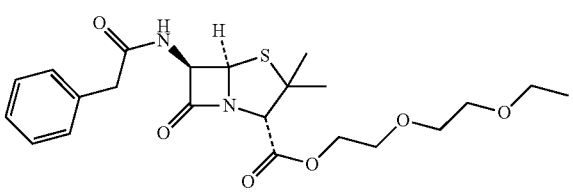

KRM-60080

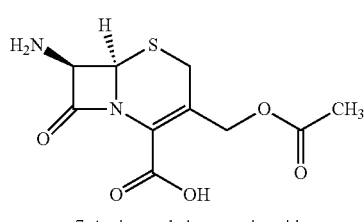

KRM-60081

7-Aminocephalosporanic acid

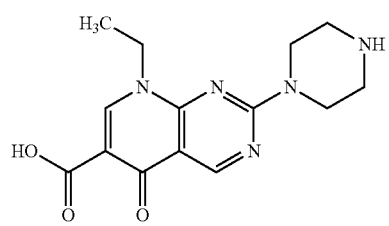 [SMILES: CCn1cc(C(=O)O)c(=O)c2cnc(N3CCNCC3)nc21]

KRM-60082

Pipemidic acid

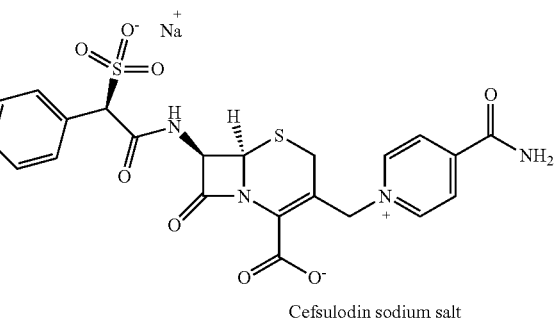

KRM-60083

Cefsulodin sodium salt

-continued

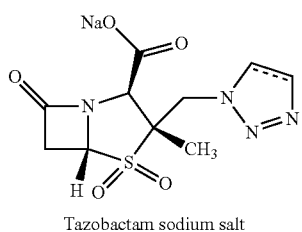

Tazobactam sodium salt

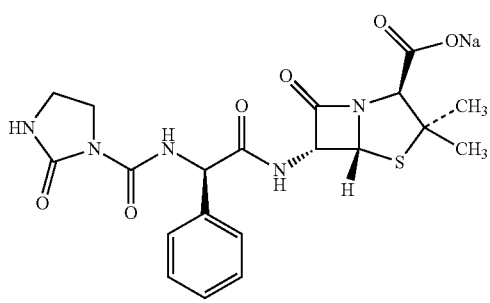

Azlocillin sodium salt

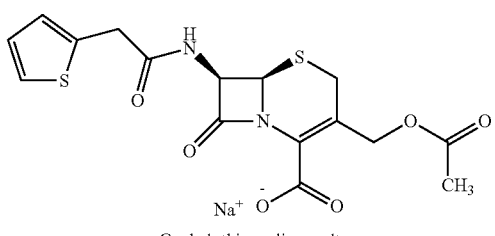

Cefotaxime sodium salt

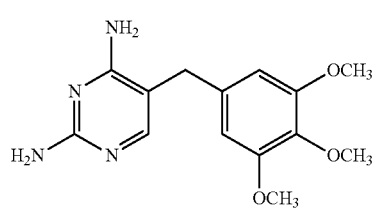 [SMILES: COc1cc(Cc2cnc(N)nc2N)cc(OC)c1OC]

Cephalothin sodium salt

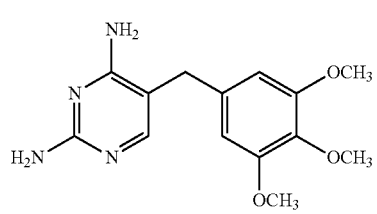

Trimethorpim

As shown in FIGS. 7 and 8, it could be confirmed that treatment with the KRM-60077 to KRM-60088 compounds increased the hardness and/or the tension of the pancreas compared to those of the control group, and particularly, treatment with the KRM-60077, KRM-60078, KRM-60080, KRM-60081, KRM-60082 and KRM-60088 compounds increased both the hardness and tension of the pancreas to significant levels.

This suggests that the compounds according to the present invention exhibited the effect of significantly increasing the tension of the pancreas and also increased the hardness of the pancreas.

The above experimental results suggest that when various modified compounds (derivatives) based on the structures of antibiotics that increase the tension and/or hardness of the pancreas are synthesized according to the present invention, compounds that effectively increase the function of the pancreas can be obtained. In addition, it can be seen that when the pancreas is treated with the compounds of the present invention, obtained as described above, the hardness and tension of the pancreas can temporarily increase, and thus the efficiency of suturing of the pancreas in surgical operations such as pancreaticoduodenectomy can increase, and furthermore, pancreatic leakage can also be prevented.

INDUSTRIAL APPLICABILITY

The present invention relates to compounds capable to temporarily hardening soft tissue for surgical suturing of the soft tissue.

The invention claimed is:

1. A compound or a pharmaceutically acceptable salt or hydrate thereof, wherein the compound is selected from the group consisting of the following compounds:
   1) Cyclohexylmethyl (2S,5R,6R)-3,3-dimethyl-7-oxo-6-(2-phenylacetamido)-4-thia-1-azabicyclo[3.2.0]heptane-2-carboxylate;
   2) 3-(tert-butoxy)-3-oxopropyl (2S,5R,6R)-3,3-dimethyl-7-oxo-6-(2-phenylacetamido)-4-thia-1-azabicyclo[3.2.0]heptane-2-carboxylate;
   3) 2-fluorobenzyl (2S,5R,6R)-3,3-dimethyl-7-oxo-6-(2-phenylacetamido)-4-thia-1-azabicyclo[3.2.0]heptane-2-carboxylate; and
   4) 2-(2-ethoxyethoxy)ethyl (2S,5R,6R)-3,3-dimethyl-7-oxo-6-(2-phenylacetamido)-4-thia-1-azabicyclo[3.2.0]heptane-2-carboxylate.

2. A pharmaceutical composition for hardening soft tissue, comprising, as an active ingredient a compound according to claim 1.

3. The pharmaceutical composition of claim 2, wherein the soft tissue is one or more tissues selected from the group consisting of pancreas, liver, nerve, ligament, serosa, myofascia, intervertebral disc, and blood vessel.

4. A pharmaceutical composition for preventing pancreatic leakage, comprising, as an active ingredient a compound according to claim 1.

5. A method for preparing a compound according to claim 1, comprising the steps of:
   dissolving a compound represented by the following formula 10 and 18-crown-6 (1,4,7,10,13,16-hexaoxacyclooctadecane) in an organic solvent; and
   adding an alkyl bromide to the dissolved solution, followed by stirring, thereby synthesizing a compound of claim 1:

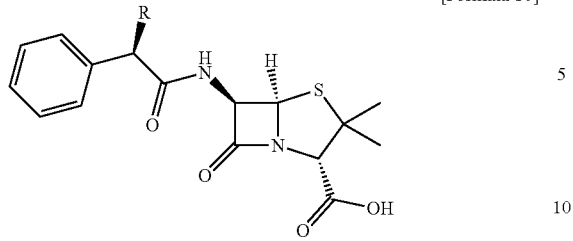
[Formula 10]
wherein R is hydrogen or N(R')(R"), and
R' and R" are each independently hydrogen or a C1-6 alkenyl group
wherein an alkyl bromide is one or more selected from the group consisting of (bromomethyl)cyclohexane, tert-butyl bromopropionate, 2-fluorobenzyl bromide and 2-(2-ethoxyethoxy)ethyl bromide.
* * * * *